(12) United States Patent
Wakshull et al.

(10) Patent No.: US 6,630,310 B1
(45) Date of Patent: Oct. 7, 2003

(54) ASSAY FOR BINDING BETWEEN CARBOHYDRATE AND GLYCOLIPID

(75) Inventors: Eric Wakshull, Princeton, MA (US); William M. Mackin, Charlton, MA (US); Janet Zimmerman, Harvard, MA (US)

(73) Assignee: Biopolymer Engineering Pharmaceutical, Inc., St. Paul, MN (US)

( * ) Notice: Subject to any disclaimer, the term of this patent is extended or adjusted under 35 U.S.C. 154(b) by 0 days.

(21) Appl. No.: 09/183,676

(22) Filed: Oct. 30, 1998

Related U.S. Application Data

(63) Continuation of application No. PCT/US97/07445, filed on May 1, 1997, which is a continuation-in-part of application No. 08/797,696, filed on Jan. 31, 1997, now Pat. No. 6,110,692, which is a continuation-in-part of application No. 08/664,173, filed on Jun. 14, 1996, now Pat. No. 6,090,938, which is a continuation-in-part of application No. 08/637,934, filed on May 1, 1996, now abandoned.

(51) Int. Cl.[7] .................. G01N 33/92; G01N 33/569; G01N 33/566
(52) U.S. Cl. .................. 435/7.1; 435/7.2; 435/4; 436/501; 436/503; 536/1.11; 536/123.1; 536/123.12; 536/55.1
(58) Field of Search .................. 435/7.2, 4, 7.1; 536/123.1, 123.12, 55.1, 1.11; 436/501, 503

(56) References Cited

U.S. PATENT DOCUMENTS

| | | |
|---|---|---|
| 5,032,401 A | 7/1991 | Jamas et al. |
| 5,089,479 A | 2/1992 | Krivan et al. |
| 5,156,948 A | 10/1992 | Christensen et al. |
| 5,217,715 A | 6/1993 | Krivan et al. |
| 5,225,330 A | 7/1993 | Ginsburg et al. |
| 5,242,800 A * | 9/1993 | Jimenez |
| 5,266,461 A | 11/1993 | Tanaka et al. |
| 5,386,027 A | 1/1995 | Krivan et al. |
| 5,389,521 A | 2/1995 | Krivan et al. |
| 5,389,547 A | 2/1995 | Tanaka et al. |
| 5,488,040 A | 1/1996 | Jamas et al. |
| 5,529,904 A | 6/1996 | Ginsburg et al. |
| 5,550,030 A | 8/1996 | Tanaka et al. |
| 5,571,683 A | 11/1996 | Nakajima et al. |

FOREIGN PATENT DOCUMENTS

| | | | |
|---|---|---|---|
| EP | 0133170 | 2/1985 | .......... A61K/31/70 |
| EP | 0 598 903 | 6/1994 | |
| EP | 0 805 161 | 11/1997 | |
| JP | 2250834 | 10/1990 | .......... A61K/37/20 |
| JP | 04 346791 | 12/1992 | |
| JP | 8053488 | 2/1996 | .......... A61K/31/70 |
| WO | 91/03495 | 3/1991 | |
| WO | 94/04163 | 3/1994 | |
| WO | 97/41439 | 11/1997 | |

OTHER PUBLICATIONS

Czop et al., "Perturbation of β–Glucan Receptors on Human Neutrophils Initiate Phagocytosis and Leukotriene B$_4$ Production", *J. Immunol.*, 141(9):3170–3176 (1988).

G. Abel and J.K. Czop, "Stimulation of Human Monocyte β–Glucan Receptors by Glucan Particles Induces Production of TNF–α and IL–1β", *Int. J. Immunopharmac.*, 14(8):1363–1373 (1992).

Doita et al., "Effect of Soluble Aminated β–1,3–D–Polyglucose on Human Monocytes: Stimulation of Cytokine and Prostaglandin E$_2$ Production but Not Antigen–Presenting Function", *J. Leuk. Biol.* 49:342–351 (1991).

Cain et al., "Role of Complement Receptor Type Three and Serum Opsonins in the Neutrophil Response to Yeast", *Complement*, 4:75–86 (1987).

Gallin et al., "Comparative Effects of Particulate and Soluble Glucan on Macrophages of C3H/HeN and C3H/HeJ Mice", *Int. J. Immunopharmac.*, 14(2):173–183 (1992).

Brunke–Reese and Mackin, "Enhanced Nitric Oxide (NO) Production by Peritoneal Macrophages Isolated From Rats Treated With PGG–glucan, (BETAFECTIN™)", *FASEB J.*, 8:A216, Abstract No. 1244 (1994).

Poutsiaka et al., "Cross–Linking of the β–Glucan Receptor on Human Monocytes Results in Interluekin–1 Receptor Antagonist But Not Interluekin–1 Production", *Blood*, 82(12):3695–3700 (1993).

Wakshull et al., "Synergistic Stimulation of Myeloid Progenitor Cell Proliferation by a Novel β–Glucan and GM–CSF", *J. Cell Biochem. Suppl.*, 18A:22 (1994).

Mackin, et al. "Enhanced Microbicidal Activities of Human Peripheral Blood Monocytes and Neutrophils (PMN) After Pre–treatment with PGG–glucan, (BETAFECTIN™)", *FASEB J.*, 8:A488, Abstract No. 2827 (1994).

Diamond et al., "The I Domain Is a Major Recognition Site on the Leukocyte Integrin Mac–1(CD11b/CD18) for Four Distinct Adhesion Ligands", *J. Cell. Biol.*, 120(4):1031–1043 (1993).

Wakshull et al., "Characterization PGG–Glucan Binding to a β–Glucan Receptor on Human Leukocytes", *FASEB J.*, 10:A1338, Abstract No. 1954 (1996).

J.K. Czop and J. Kay, "Isolation and Characterization of β–Glucan Receptors on Human Mononuclear Phagocytes", *J. Exp. Med.*, 173(6):1511–1520 (1991).

(List continued on next page.)

*Primary Examiner*—Lorraine Spector
*Assistant Examiner*—Claire M. Kaufman
(74) *Attorney, Agent, or Firm*—Darby & Darby

(57) ABSTRACT

A preparation containing a receptor for underivatized, aqueous soluble β(1–3)-glucan is disclosed, along with characterization of the receptor for underivatized, aqueous soluble β(1–3)-glucan. Also described are assays for identifying agents which alter the effect of underivatized, aqueous soluble β(1–3)-glucan on activation of signal transduction pathways and agents identified thereby, as well as assays for assessing the specificity of carbohydrate:glycolipid interactions.

3 Claims, 17 Drawing Sheets

OTHER PUBLICATIONS

Szabó et al., "Biochemical Properties of the Ligand–binding 20–kDa Subunit of the β–Glucan Receptors on Human Mononuclear Phagocytes", *J. Biol. Chem., 270(5)*:2145–2151 (1995).

R. Goldman, "Induction of a β–1,3–D–glucan receptor in P388D1 cells treated with retinoic acid or 1,25–dihydroxyvitamin $D_3$", *Immunology, 63(2)*:319–324 (1988).

R. Goldman, "Characteristics of the β–Glucan Receptor of Murine Macrophages", *Exp. Cell. Res., 174(2)*:481–490 (1988).

Thornton, et al., "Analysis of the Sugar Specificity and Molecular Location of the β–Glucan–Binding Lectin Site of Complement Receptor Type 3 (CD11b/CD18)", *J. Immunol., 156(3)*:1235–1246 (1996).

Konopski et al., "A Novel Immunomodulator Soluble Aminated β–1,3–D–Glucan: Binding Characteristics to Mouse Peritoneal Macrophages", *Biochem. Biophys. Acta, 1221(1)*:61–65 (1994).

Müller et al., "Receptor Binding and Internalization of a Water–Soluble (1→3)–β–D–Glucan Biologic Response Modifier in Two Monocyte/Macrophage Cell Lines", *J. Immunol., 156*:3418–3425 (1996).

Engstad and Robertsen, "Specificity of a β–Glucan Receptor on Macrophages from Atlantic Salmon (*Salmo salar L.*)", *Dev. Comp. Immunol., 18(5)*:397–408 (1994).

Muller et al., "Functional β–glucan receptor expression by a microglial cell line", *Res. Immunol., 145*:267–275 (1994).

Czop et al., "Production and Isolation of Rabbit Anti–Idiotypic Antibodies Directed Against the Human Monocyte Receptor for Yeast β–Glucans", *J. Immunol., 145(3)*:995–1001 (1990).

Bhunia et al., "Lactosylaceramide Stimulates Ras–GTP Loading, Kinases (MEK, Raf), p44 Mitogen–activated Protein Kinase, and c–fos Expression in Human Aortic Smooth Muscle Cells", *J. Biol. Chem., 271(18)*:10660–10666 (1996).

Chatterjee et al., "Role of lactosylceramide and MAP kinase in the proliferation of proixmal tubular cells in human polycystic kidney disease", *J. Lipid Research 37*:1334–1343 (1996).

S. Chatterjee, "Lactosylceramide stimulates aortic smooth muscle cell proliferation", *Biochem. and Biophy. Research Comm., 181(2)*:554–561 (1991).

S. Chatterjee, "Regulation of synthesis of lactosyceramide in normal and tumor proximal tubular cells", *Biochem. Biophys. Acta, 1167*:339–344 (1993).

Stevens et al., "Lactosylceramide in inflammatory bowel disease: a biochemical study", *Gut, 29*:580–587 (1988).

Lund–Johansen et al., "Activation of Human Phagocytes Through Carbohydrate Antigens (CD15, Sialyl–CD15, CDw17, and CDw65)", *J. Immunol., 148*:3221–3229 (1992).

Yamamoto et al., "Binding Specificity of *Lactobacillus* to Glycolipids", *Biochem. and Biophys. Research Comm., 228*:148–152 (1996).

Tsuroka et al., "Selection of a Mutant Cell Line Based on Differential Expression of Glycosphingolipid, Utilizing Anti–lactosylceramide Antibody and Complement", *J. Biol. Chem. 268(3)*:2211–2216 (1993).

Baker et al., "Glycosphingolipid Receptors for *Pseudomonas aeruginosa*", *Infec. Immun., 58(7)*:2361–2366 (1990).

Fukuda et al., "Structures of Glycosphingolipids Isolated from Huamn Granulocytes", *J. Biol. Chem., 260(2)*:1067–1082 (1985).

Strömberg et al., "Studies on the binding of bacteria to glycolipids–Two Species of *Propionibacterium* apparently recognize separate epitopes on lactose of lactosylceramide", *FEBS Letters, 232(1)*:193–198 (1988).

F. Symington, "CDw17: A Neutrophil Glycolipid Antigen Regulated by Activation", *J. Immunol., 142(8)*:2784–2790 (1989).

Backenson et al., "*Borrelia burgdorferi* Shows Specificity of Binding to Glycosphingolipids", *Infec. Immun., 63(8)*:2811–2817 (1995).

Karl–Anders Karlsson, "Animal Glycosphingolipids as Membrane Attachment Sites for Bacteria", *Annu. Rev. Biochem., 58*:309–350 (1989).

Jimenez–Lucho et al., "*Cryptococcus neoformans, Candida Albicans,* and Other Fungi Bind Specifically to the Glycosphingolipid Lactosyceramide (Galβ1–4Glcβ1–1Cer), a Possible Adhesion Receptor for Yeasts", *Infec. Immun., 58(7)*:2085–2090 (1990).

Sandberg et al., "Putative Glycoprotein and Glycolipid Polymorphonuclear Leukocyte Receptors for the *Actinomyces naeslundii* WVU45 Fimbrial Lectin", *Infec. and Immun., 63(7)*:2625–2631 (1995).

Chatterjee et al., "Accumulation of glycosphingolipids in human atherosclerotic plaque and unaffected aorta tissues", *Glycobiology, 7(1)*:57–65 (1997).

Janusz, M.J. et al., "Isolation of Soluble Yeast β–Glucans that Inhibit Human Monocyte Phagocytosis Mediated by β–Glucan Receptors," *The Journal of Immunology, 137(10)*:3270–3276 (Nov. 15, 1986).

Konopski, Z. et al., "IFN–gamma inhibits internalization of soluble aminated beta–1,3–D–glucan by macrophages and thereby down–regulates the glucan induced release of TNF–alpha and IL–1beta," *Chemical Abstracts, 121*(13): (Sep. 26, 1994).

Konopski, Z. et al., "A novel immunomodulator soluble aminated beta–1,3–D–glucan: binding characteristics to mouse peritoneal macrophages," *Chemical Abstracts, 120*(17): (Apr. 25, 1994).

Baldwin, A.S., "The NF–κB and IκB Proteins: New Discoveries and Insights", *Annu. Rev. Immunol., 14*:649–681 (1996).

James et al., "A Novel Class of Macrophage–Activating Immunomodulators", ACS Symposium Series, Polymeric Drugs and Delivery System, pp. 44–51 (Aug. 26–31, 1990).

Stewart, J. and Boggs J., "A Carbohydrate Carbohydrate Interaction between Galactosylceramide–Containing Liposomes and Cerebroside Sulfate–Containing Liposomes: Dependence on the Glycolipid Ceramide Composition," *Biochemistry, 32*:10666–10674 (1993).

Zimmerman et al., "A Novel Carbohydrate–Glycosphingolipid Interaction between a β–(1–3)–Glucan Immunomodulator, PGG–glucan, and Lactosylceramide of Human Leukocytes", *J. Biol. Chem., 273(34)*:22014–22020 (1998).

Adams et al., "PGG–Glucan Activates NK–κB–like and NF–IL–6–like Transcription Factor Complexes in a Murine Monocytic Cell Line", *J. Leukocyte Biol., 62*:865–873 (1997).

Hossain, M.A., et al., "Comparison Between Wako–WB003 and Fungitec G Tests for Detection of (1–3)–β–D–Glucan in Systemic Mycosis," *J. Clin. Laboratory Analysis*, 11:73–77 (1997); (Exhibit K).

Konopski, Z., "Interferon–γ Inhibits Endocytosis of Soluble Animated β–1,3–D–Glucan and Neutral Red in Mouse Peritoneal Macrophages," *Journal of Interferon and Cytokine Research* 15:597–603 (1995).

Mills, A. and Dugan, M.J., "Orphan seven transmembrane domain receptors: reversing pharmacology," *Trends in Biotechnology* 12:47–49 (1994).

Miyazaki, T., et al., "Plasma (1–3)–β–D–Glucan and Fungal Antigenemia in Patients with Candidemia, Aspergillosis, and Cryptococcosis," *J. of Clin. Microbiology*, 33(12):3115–3118 (1995); (Exhibit L).

Mori, T., et al., "Evaluation of Plasma (1–3)–β–D–Glucan Measurement by the Kinetic Turbidimetric Limulus Test, for the Clinical Diagnosis of Mycotic Infections," *Eur. J. Clin. Chem. Clin. Biochem.*, 35(7):553–560 (1997); (Exhibit M).

Morita, T., et al., "A New (1–3)–β–D–Glucan Mediated Coagulation Pathway Found in Limulus Amebocytes," *Elsevier/North–Holland Biomedical Press*, 129(2):318–321 (1981); (Exhibit N).

Schütze, S., et al., "The role of diacylglycerol and ceramide in tumor necrosis factor and interleukin–1 signal transduction," *J. of Leukocyte Biology*, 56:533–541 (1994).

Tamura, H., et al., "Plasma (1–3)–β–D–Glucan Assay and Immunohistochemical Staining of (1–3)–β–D–Glucan in the Fungal Cell Walls Using a Novel Horseshoe Crab Protein (T–GBP) that Specifically Binds to (1–3)–β–D–Glucan," *J. of Clin. Laboratory Analysis*, 11:104–109 (1997); (Exhibit O).

Ullrich, A. and Schlessinger, J., "Signal Transduction by Receptors with Tyrosine Kinase Acivity," *Cell* 62:203–212 (1990).

Williams, D.L. and Quillen, J.H., "Overview of (1–3)–β–D–Glucan Chemistry, Immunology and Toxicology," Paper presented at the Beltwide Cotton Conference, Nashville, TN (1996).

Karlsson, Chemistry and Physics of Lipids 42:153–172, 1986.*

Jamas et al., ACS Symposium series, Polymeric Drugs and Drug Delivery System, pp. 44–51, 1991.*

Stewart et al., Biochemistry 32:10666–10674, 1993.*

Jimenez–Lucho et al., Infection and Immunity 58(7):2085–90, Jul. 1990.*

* cited by examiner control

PGG-Glucan dextran control

PGG-Glucan dextran

ASSAY FOR BINDING BETWEEN CARBOHYDRATE AND GLYCOLIPID

RELATED APPLICATIONS

This application is a continuation of PCT/US97/07445, filed May 1, 1997, which is a continuation-in-part application of U.S. Ser. No. 08/797,696, filed Jan. 31, 1997, issued as U.S. Pat. No. 6,110,692 on Aug. 29, 2000, which is a continuation-in-part application of U.S. Ser. No. 08/664, 173, filed Jun. 14, 1996, issued as U.S. Pat. No. 6,090,938 on Jul. 18, 2000, which is a continuation-in-part of U.S. Ser. No. 08/637,934, filed May 1, 1996, now abandoned. The teachings of the prior applications are incorporated herein in their entirety.

BACKGROUND OF THE INVENTION

Underivatized, aqueous soluble β(1–3)-glucan (also known as PGG-Glucan or Betafectin®) is a novel and unique soluble β-glucan manufactured through a proprietary process. The biological activity of this molecule is clearly distinguishable from particulate or other soluble β-glucans. Numerous laboratories have reported direct induction of arachidonic acid metabolites (Czop et al., *J. Immunol.* 141(9):3170–3176 (1988)), cytokines (Abel and Czop, *Intl. J. Immunopharmacol.* 14(8):1363–1373 (1992); Doita et al., *J. Leuk. Biol.* 14(2):173–183 (1991)) and oxidative burst (Cain et al., *Complement*, 4:75–86 (1987); Gallin et al., *Int. J. Immunopharmacol.* 14(2):173–183 (1992)) by both particulate and soluble forms of β-glucans. In contrast, underivatized, aqueous soluble β(1–3)-glucan does not directly activate leukocyte functions such as oxidative burst activity (Mackin et al., *FASEB J.* 8:A216 tokine secretion (Putsiaka et al., Blood 82:3695–3700 (1993)) or proliferation (Wakshull et al., *J. Cell. Biochem. suppl.* 18A:22 (1994)). Instead, underivatized, aqueous soluble β(1–3)-glucan primes cells for activation by secondary stimuli (Mackin et al. (1994); Brunke-Reese and Mackin, *FASEB J.* 8:A488 (1994); and Wakshull et al. (1994)).

The biological activity of β-glucans is mediated through specific receptors located on target cells. Several groups of investigators have described receptors which bind particulate β-glucan preparations. For example, receptors for particulate β-glucans (e.g., zymosan-like particles) have been described by Czop and colleagues (Czop and Kay, *J. Exp. Med.* 173:1511–1520 (1991); Szabo et al., *J. Biol. Chem.* 270:2145–2151 (1995)) and Goldman (*Immunology* 63(2):319–324 (1988); *Exp. Cell. Res.* 174(2):481–490 (1988)). The leukocyte complement receptor 3 (CR3, also known as MAC 1 or CD11b/CD18) has been shown to have the capacity to bind both particulate and some soluble β-glucans, as well as other polysaccharides (Thornton et al., *J. Immunol.* 156:1235–1246 (1996)). A soluble aminated β-glucan preparation has been shown to bind to murine peritoneal macrophages (Konopski et al., *Biochim. Biophys. Acta* 1221:61–65 (1994)), and a phosphorylated β-glucan derivative has been reported to bind to monocyte cell lines (Muller et al., *J. Immunol.* 156:3418–3425 (1996)). The ability of salmon macrophages (Engstad and Robertsen, *Dev. Comp. Immunol.* 18(5):397–408 (1994)) and brain microglial cells (Muller et al., *Res. Immunol.* 145:267–275 (1994)) to phagocytose β-glucan particles, presumably through a receptor-mediated process, has also been described.

Unfortunately, each group has utilized β-glucan preparations varying widely in their source, method of preparation, purity and characterization. In addition, different cell types and species, both primary and established cell lines, and different functional read-outs have been used. The relationship between the various receptors described by these investigators has, therefore, not been defined, although it is clear that the receptor described by Czop is not CR3 (Szabo et al. (1995)).

SUMMARY OF THE INVENTION

This invention pertains to the discovery that underivatized, aqueous soluble β(1–3)-glucan specifically binds to a novel receptor located on human leukocyte membranes (HLM). As described herein, a radiolabeled underivatized, aqueous soluble β(1–3)-glucan was used to measure the binding of this β-glucan to membrane receptors derived from human leukocytes as well as various murine and human cell lines. The receptor for underivatized, aqueous soluble β(1–3)-glucan shows specific and saturable binding to membranes and is highly selective for a subclass of soluble β-glucans. Results of work described herein characterize this receptor for underivatized, aqueous soluble β(1–3)-glucan and clearly differentiate it from previously described β-glucan receptors for either particulate or soluble β-glucans, while revealing important information about the mechanism of underivatized, aqueous soluble β(1–3)-glucan biological activity.

This invention also pertains to a method of altering (e.g., activating or deactivating) signal transduction pathways, for example through modulation of one or more transcriptional regulatory factors in receptor-positive cells, i.e., cells which contain the receptor for underivatized, aqueous soluble β(1–3)-glucan. In one embodiment of the invention, the signal transduction pathway is modulated or regulated by one or more transcriptional regulatory factors from the NF-κB and/or NF-IL6 and/or jun/fos families of transcriptional regulatory factors. For example, the transcriptional regulatory factor can be NF-κB, NF-IL6 or AP-1.

Other signal transduction pathways which can be altered by the methods of the present invention include the ras/raf-1/MAP kinase pathway, the G-protein/phospholipase C/protein kinase C pathway, the JAK/STAT pathway, the phospholipase A pathway, G-protein/phospholipase D/phosphatidic acid pathway and the c-AMP-dependent pathway. In each pathway, an appropriate activator or indicator of the signal pathway is activated by binding of underivatized, aqueous soluble β(1–3)-glucan to its receptor, and modulation of this binding can alter the corresponding signal transduction.

According to the method of the present invention, the activity of the receptor for underivatized, aqueous soluble β(1–3)-glucan is activated through binding of an underivatized, aqueous soluble β(1–3)-glucan, whereby a signal transduction process is activated such that one or more transcriptional regulatory factors (e.g., from the NF-κB, NF-IL6 or jun/fos families) are activated. Activation of these transcriptional regulatory factors can be used to measure the activation of the associated signal transduction pathway. Activation of the receptor can comprise, among others, an alteration in the receptor conformation, formation of a ligand-receptor complex, or alteration of the ligand-receptor complex. Alternatively, the activity of the receptor can be initiated by an agent which mimics the binding and activation ability of an underivatized, aqueous soluble β(1–3)-glucan. In a particular embodiment, the transcriptional regulatory factor is activated as a result of ligand binding. In another embodiment, the activity of the transcriptional regulatory factor is decreased, either partially or totally, by the binding of an agent to the receptor (and thus excludes the underivatized, aqueous soluble β(1–3)-glucan), but lacks the ability to activate the receptor.

The invention also pertains to an assay for identifying agents which alter (e.g., increase or decrease) the binding of underivatized, aqueous soluble β(1–3)-glucan to its receptor.

The assay comprises combining radiolabeled underivatized, aqueous soluble β(1–3)-glucan, the receptor for underivatized, aqueous soluble β(1–3)-glucan, and an agent to be tested, under conditions suitable for binding of underivatized, aqueous soluble β(1–3)-glucan to its receptor. The extent of binding of underivatized, aqueous soluble β(1–3)-glucan to its receptor in the presence of the agent to be tested is determined and compared with the extent of binding in the absence of the agent to be tested; a difference in the extent of binding indicates that the agent alters the binding of underivatized, aqueous soluble β(1–3)-glucan to its receptor. An increase in the extent of binding in the presence of the agent indicates that the agent enhances, i.e., prolongs or increases, binding or is an agonist of the receptor for underivatized, aqueous soluble β(1–3)-glucan. A decrease in the extent of binding in the presence of the agent indicates that the agent diminishes, i.e., shortens or decreases, binding or is an antagonist of the receptor for underivatized, aqueous soluble β(1–3)-glucan. The invention also relates to agents identified by assays described herein, and accordingly, relates to agonists and antagonists of underivatized, aqueous soluble β(1–3)-glucan activity.

The present invention also pertains to a novel assay for identifying agents which alter (e.g., increase or decrease) the effect of underivatized, aqueous soluble β(1–3)-glucan on cellular signal transduction pathways, such as activation of transcriptional regulatory factors. This assay comprises combining underivatized, aqueous soluble β(1–3)-glucan, the receptor for underivatized, aqueous soluble β(1–3)-glucan and an agent to be tested under conditions in which binding of underivatized, aqueous soluble β(1–3)-glucan to its receptor occurs (i.e., conditions suitable for binding of underivatized, aqueous soluble β(1–3)-glucan to the receptor for underivatized, aqueous soluble β(1–3)-glucan). Binding of underivatized, aqueous soluble β(1–3)-glucan to its receptor activates the receptor, which in turn activates a signal transduction as exemplified or measured by a modulation of one or more transcriptional regulatory factors such as those from the NF-κB, NF-IL6 or jun/fos families. The extent of activation of the selected transcriptional regulatory factor in the presence of an agent to be tested is determined and compared with the extent of activation of the selected transcriptional regulatory factor in the absence of the agent to be tested; a difference in the extent of activation indicates that the agent alters the effect of underivatized, aqueous soluble β(1–3)-glucan on activation of the transcriptional regulatory factor. An increase in the activation of the transcriptional regulatory factor in the presence of the agent indicates that the agent enhances, i.e., prolongs or increases, the activation. A decrease in the activation of the transcriptional regulatory factor in the presence of the agent indicates that the agent diminishes, i.e., shortens or decreases, the activation.

The assays and methods of the present invention can be used to identify agents and drugs for use in treatment of infectious disease, inflammation, autoimmune diseases, ischemia reperfusion injury, cancer, asthma and hypersensitivity disorders. The assays and methods described herein can also be used to identify drugs which prolong the underivatized, aqueous soluble β(1–3)-glucan effect, and therefore can be used in any therapeutic or prophylactic application in which underivatized, aqueous soluble β(1–3)-glucan can be used, such as for immunomodulation, hematopoiesis, prevention and treatment of infectious disease, platelet production, peripheral blood precursor cell mobilization and wound healing. These agents or drugs act to enhance the effects of underivatized, aqueous soluble β(1–3)-glucan by, for example, prolonging the binding of the glucan to its receptor or the effects thereof.

The present invention also relates to agents or drugs, such as, but not limited to, peptides or small organic molecules designed with reference to the binding site for underivatized, aqueous soluble β(1–3)-glucan on the receptor for underivatized, aqueous soluble β(1–3)-glucan. In one embodiment, such agents or drugs can be designed to mimic the activity of the receptor binding site in that they bind underivatized, aqueous soluble β(1–3)-glucan, thus decreasing the amount of the β(1–3)-glucan which is available for binding to the receptor and decreasing the activation of downstream events such as signal transduction. The present invention also pertains to an agonist or mimic of underivatized, aqueous soluble β(1–3)-glucan activity with respect to its binding and activation of the receptor for underivatized, aqueous soluble β(1–3)-glucan. Alternatively, the drug or agent can be designed to bind the receptor binding site, rendering it unavailable for binding by underivatized, aqueous soluble β(1–3)-glucan; the present invention also relates to antagonists of underivatized, aqueous soluble β(1–3)-glucan binding activity.

The work described herein has application to many areas. For example, it can be used in the monitoring of the underivatized, aqueous soluble β(1–3)-glucan manufacturing process and product characterization for commercial release, to measure β-glucans in fluids, to assess and determine structure-activity relationships of agents that interact with the receptor for the underivatized aqueous soluble β(1–3)-glucan. Additionally, this work has application to the targeted delivery of various agents, including drugs and small molecules, to receptor-positive cells such as peripheral polymorphonuclear leukocytes, monocytes, macrophages and epithelial cells. The results described herein can also be used in purification schemes to enrich for both receptor-positive cells and receptor-negative cells, as well as in the generation of anti-receptor antibodies for diagnostic purposes.

BRIEF DESCRIPTION OF THE DRAWINGS

FIG. 2A shows the total binding (continuous line, closed circles), non-specific binding (dashed line, open squares) and specific binding (dashed line, open diamonds) of varying concentrations of radioactively labeled underivatized, aqueous soluble β(1–3)-glucan. Data points represent the mean±standard deviation of triplicate samples. FIG. 2B depicts a Scatchard analysis of the binding data.

FIG. 16A shows the results for nuclear transcription factor NF-kB. FIG. 16B shows the results for nuclear transcription factor NF-IL6. In both instances, purified human neutrophils were incubated with or without underivatized, aqueous soluble β(1–3)-glucan (3 μg/ml) or dextran (3 μg/ml) for 60 minutes at 37° C. Nuclear extracts were prepared and protein/DNA complex formation assessed by electrophoretic mobility shift assay (EMSA). Underivatized, aqueous soluble β(1–3)-glucan increased the binding of nuclear extract proteins to an NF-kB or NF-IL6 specific 32P-labeled oligonucleotide probe relative to extracts from either control or dextran-treated neutrophils. The horizontal arrow indicates the location of the protein/DNA complex.

DETAILED DESCRIPTION OF THE INVENTION

Figure 1:
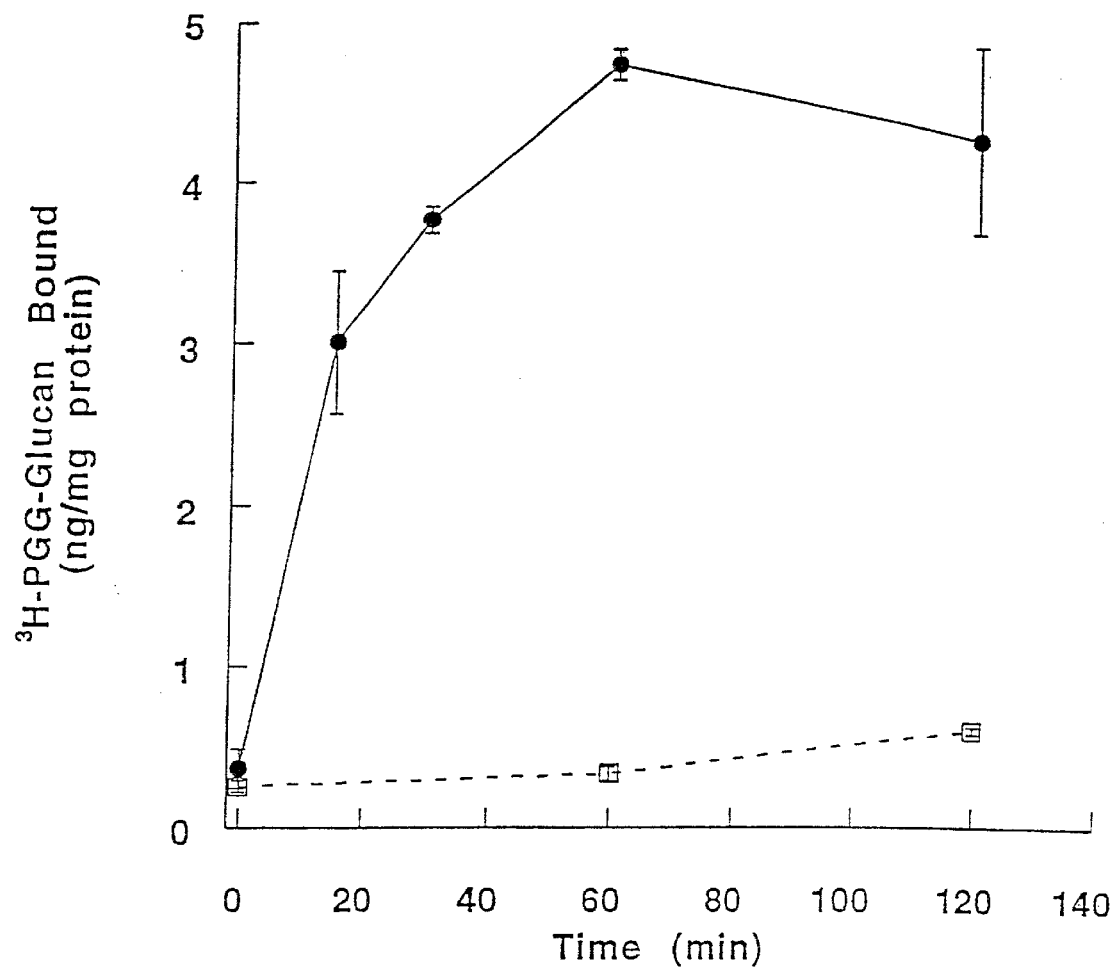
FIG. 1 is a graphic depiction of the time course of radioactively labeled underivatized, aqueous soluble β(1–3)-glucan binding to human leukocyte membranes. Total binding is indicated by a continuous line with closed circles and non-specific binding is indicated by a dashed line with open squares. The data points represent the mean±standard deviation of triplicate samples.

This invention pertains to the discovery that underivatized, aqueous soluble β(1–3)-glucan (see U.S. Ser. No. 07/934,015, filed Aug. 21, 1992, the teachings of which are incorporated herein by reference) specifically binds to a novel receptor located on human leukocyte membranes (HLM). Underivatized, aqueous soluble β(1–3)-glucans are also described in U.S. Ser. Nos. 08/400,488, 08/432,303, 07/934,015, 08/373,251 and 08/469,233 and U.S. Pat. Nos. 5,322,841, 5,488,040 and 5,532,223. Results of work described herein characterize this receptor for underivatized, aqueous soluble β(1–3)-glucan (also known as PGG-glucan) and clearly differentiate it from previously described β-glucan receptors, while revealing important information about the mechanism of underivatized, aqueous soluble β(1–3)-glucan biological activity.

The receptor for underivatized, aqueous soluble β(1–3)-glucan is located primarily in human blood cells, specifically the neutrophil and mononuclear leukocytes (monocytes and lymphocytes). As used herein, "receptor" is intended to encompass a traditional receptor molecule as well as a binding site; such a binding site can have an effect of its own or may induce or activate a second molecule or binding site to produce an effect (also known as "unmasking" of a second site; Sandberg et al., Infect. Immun. 63(7):2625–2631 (1995)). As used herein, "receptor" is also intended to include compounds which have an affinity for underivatized, aqueous soluble β(1–3)-glucan; these compounds can be receptor mimics or receptor analogues, and can be isolated from a naturally-occurring source or can be chemically or synthetically produced. The receptor for underivatized, aqueous soluble β(1–3)-glucan exhibits selectivity for β(1–3)-glucans and particularly for underivatized, aqueous soluble β(1–3)-glucan in the triple helix conformation.

A variety of polysaccharides were tested for their ability to compete for radioactively labeled underivatized, aqueous soluble β(1–3)-glucan binding. The receptor for underivatized, aqueous soluble β(1–3)-glucan distinguishes β(1–3)-glucans from non-β(1–3)-glucans such as dextran, mannan, glycogen and lipopolysaccharide (LPS) (Table 1). The underivatized, aqueous soluble β(1–3)-glucan sample represents non-specific binding. Aminated glucan was prepared by reductive amination of curdlan and provided by Dr. Rolph Seljelid (University of Tromsφ, Tromsφ, Norway). For the exoglucanase sample, unlabeled underivatized, aqueous soluble β(1–3)-glucan was treated with exoglucanase, then used to compete with radioactively labeled underivatized, aqueous soluble β(1–3)-glucan binding. The anti-idiotype antibody was a rabbit monoclonal anti-idiotype antibody developed against a mouse monoclonal anti-laminarin antibody (Czop et al., J. Immunol. 145(3):995–1001 (1990)). The observation that the β(1–3)-glucans, laminarin and aminated glucan do not inhibit radioactively labeled underivatized, aqueous soluble β(1–3)-glucan binding to the receptor located on the human leukocyte membranes indicates selectivity among this group of polysaccharides also.

TABLE 1

Effect of Various Incubation Conditions on
³H-PGG-Glucan Binding to Human Leukocyte Membranes

| Addition/Treatment | Concentration | Source | % Control Binding | % CV |
|---|---|---|---|---|
| PGG-Glucan | 0.1 mg/ml | ABT | 22 | 5 |
| Dextran | 1 mg/ml | Sigma | 88 | 12 |
| Mannan | 1 mg/ml | Sigma | 88 | 5 |
| Laminarin | 1.0 mg/ml | Calbiochem | 83 | 5 |
| Glycogen | 0.1 mg/ml | Sigma | 134 | 20 |
| Lipopolysaccharide | 0.1 mg/ml | Sigma | 89 | 16 |
| Aminated Glucan | 0.1 mg/ml | R. Seljelid | 111 | 1 |
| EDTA | 5 mM | Sigma | 82 | 13 |
| EGTA | 5 mM | Sigma | 87 | 0.1 |
| Exoglucanase | 0.26 U/ml | ABT | 92 | 5 |
| anti-idiotype | 10 µg/ml | J. Czop | 88 | 7 |
| anti-CR3 | 28 µg/ml | Becton-Dickinson | 123 | 19 |

Figure 6:
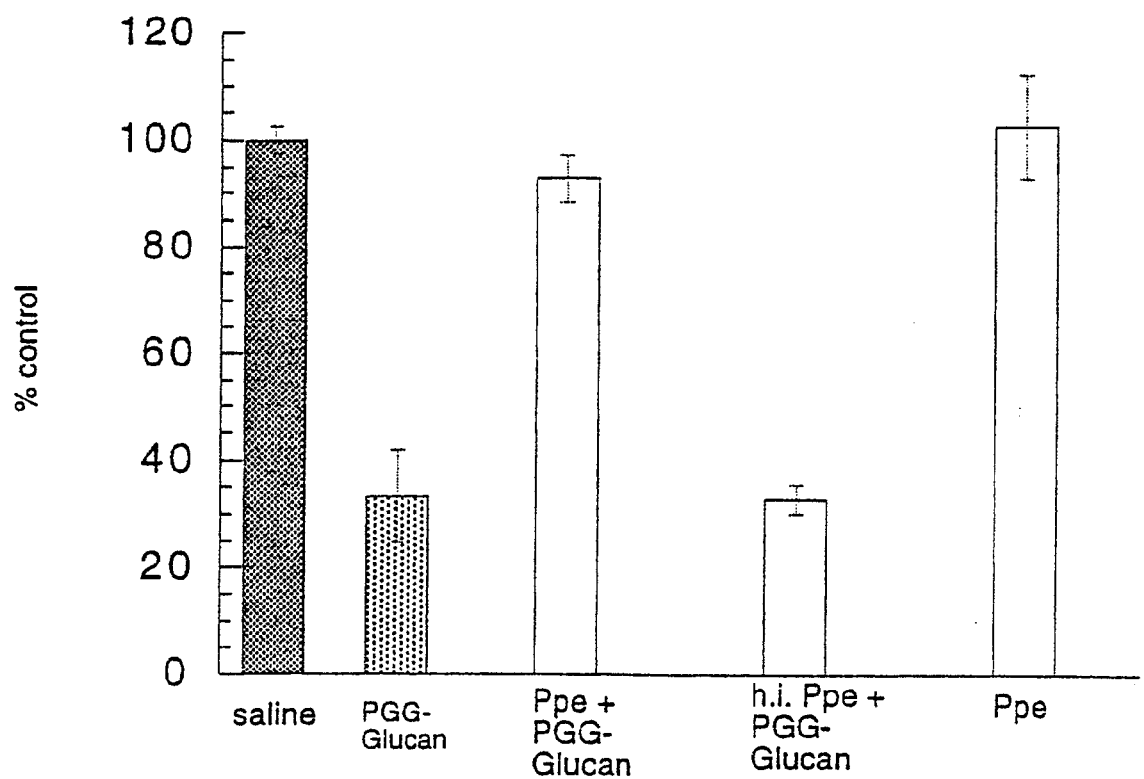
FIG. 6 is a graph of the effect of exoglucanase treatment of underivatized, aqueous soluble β(1–3)-glucan on competitive binding.

Unlabeled underivatized, aqueous soluble β(1–3)-glucan (1 mg) was treated with 0.13 units of 1,3-exoglucanase (partially purified from *Penicillium pinophilum*) at 50° C. overnight either before or after heat inactivation of the enzyme. Human leukocytes were then incubated with radioactively labeled underivatized, aqueous soluble β(1–3)-glucan in the presence or absence of unlabeled underivatized, aqueous soluble β(1–3)-glucan (0.2 mg/ml). As a control, the exoglucanase was added to the binding reaction in the absence of unlabeled underivatized, aqueous soluble β(1–3)-glucan. Results are shown in FIG. 6.

Figure 7:
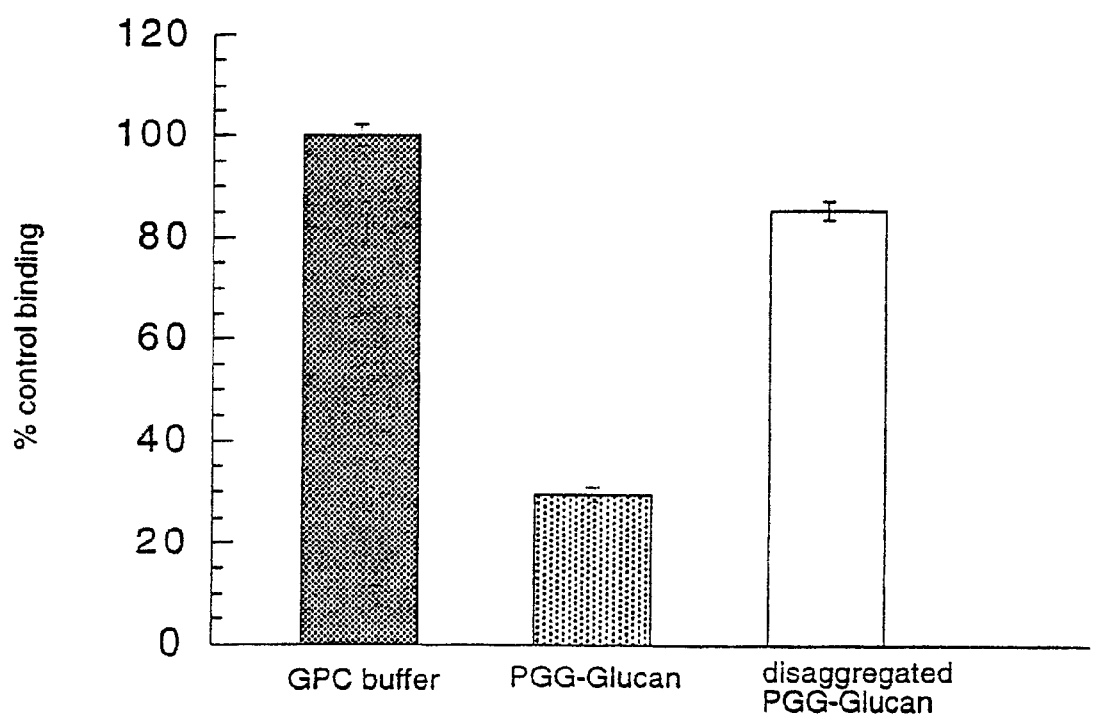
FIG. 7 is a graph of the effect of NaOH treatment on the ability of underivatized, aqueous soluble β(1–3)-glucan to compete for binding.

Underivatized, aqueous soluble β(1–3)-glucan (1 mg/ml) was treated with 1 M NaOH for 30 minutes at room temperature, then diluted to 0.1 mg/ml. Gel permeation chromatography-isolated fractions containing disaggregated underivatized, aqueous soluble β(1–3)-glucan were assayed for competition of radioactively labeled underivatized, aqueous soluble β(1–3)-glucan binding. Both underivatized, aqueous soluble β(1–3)-glucan and disaggregated underivatized, aqueous soluble β(1–3)-glucan were used at 23 µg/ml in the binding assay. Results are shown in FIG. 7.

Figure 8:
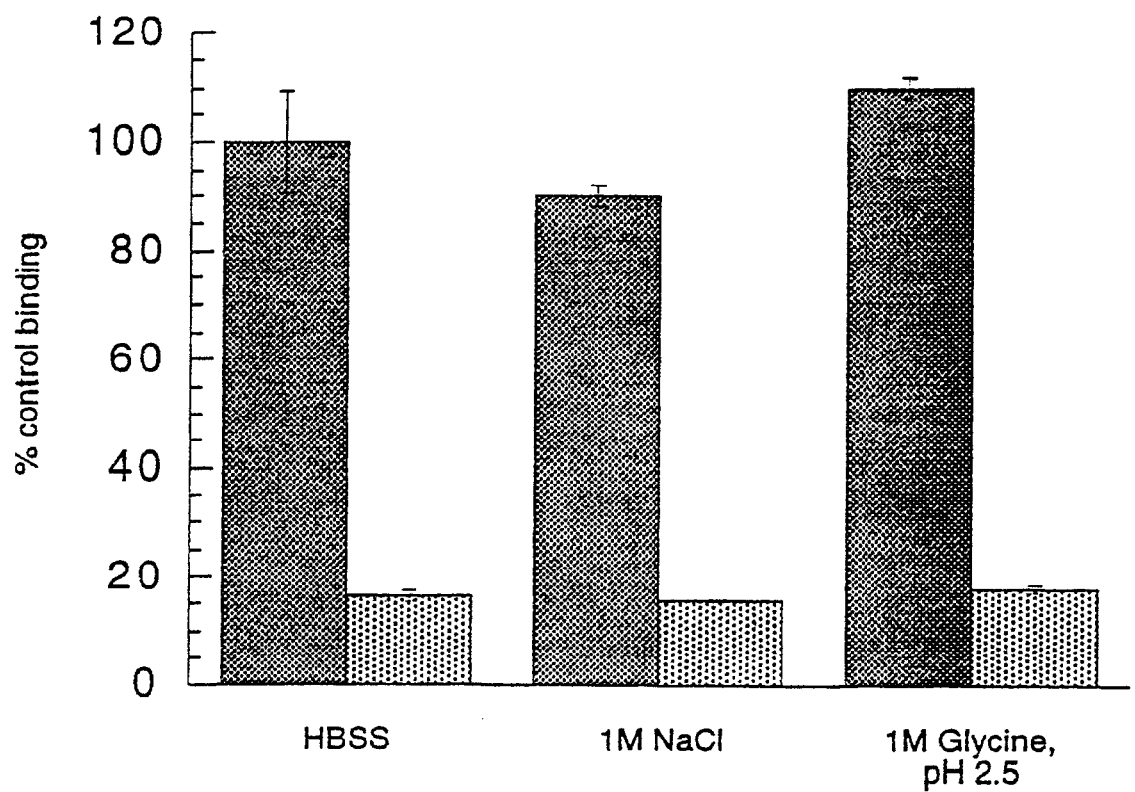
FIG. 8 is a graph of the effect on binding of treatment of human leukocyte membranes with glycine/pH 2.5 or 1 M NaCl. Solid columns indicate the saline control; stippled columns indicate underivatized, aqueous soluble β(1–3)-glucan sample.

Human leukocyte membranes were incubated on ice for one hour in the presence of HBSS, 0.1 M glycine/pH 2.5 or 1 M NaCl, then pelleted by centrifugation at 180,000×g for 60 minutes at 4° C., washed, and used in the binding assay. The supernatants of the 180,000×g spin were analyzed for protein content (BCA reagent, Pierce), which showed 12% and 20% of the total protein was released from the salt and glycine treated membranes, respectively, over or above the HBSS control. The results (shown in FIG. 8) indicate that high salt and low pH did not alter binding of underivatized, aqueous soluble β(1–3)-glucan to human leukocyte membranes. Thus, binding is unaffected by conditions that remove peripheral proteins, suggesting that the binding site is unlikely to be a peripheral protein.

Figure 9:
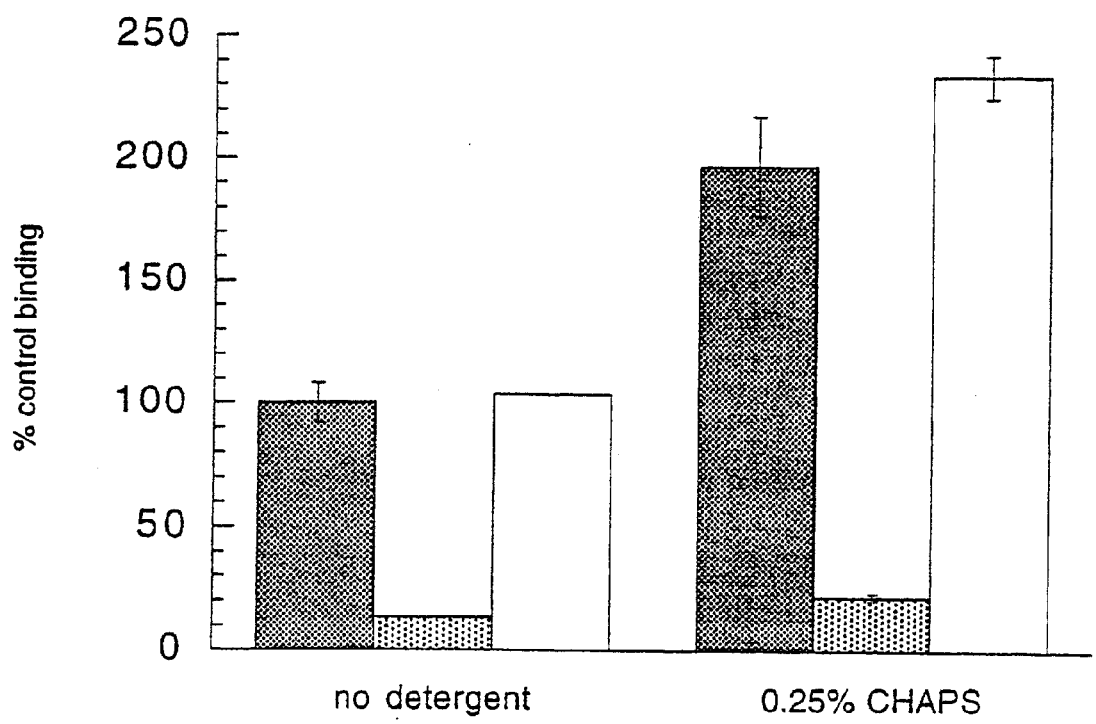
FIG. 9 is a graph of the effect on binding of pretreatment of human leukocyte membranes with CHAPS. Solid columns indicate the saline control; stippled columns indicate underivatized, aqueous soluble β(1–3)-glucan sample. Open columns indicate the dextran sample.

Human leukocyte membranes were incubated in HBSS with or without 0.25% CHAPS for 5 minutes on ice, followed by centrifugation at 180,000×g, 4° C. for 45 minutes. Pellets were used in a binding assay with underivatized, aqueous soluble β(1–3)-glucan or dextran (avg. MW 71,000, Sigma Chemical Co., MO) as indicated at 1 mg/ml final concentration. Results are shown in FIG. 9. A similar enhancement of specific binding was seen with the detergent octylglucoside. These results indicate that the binding site probably contains regions associated with the hydrophobic portion of the membranes.

Figure 10:
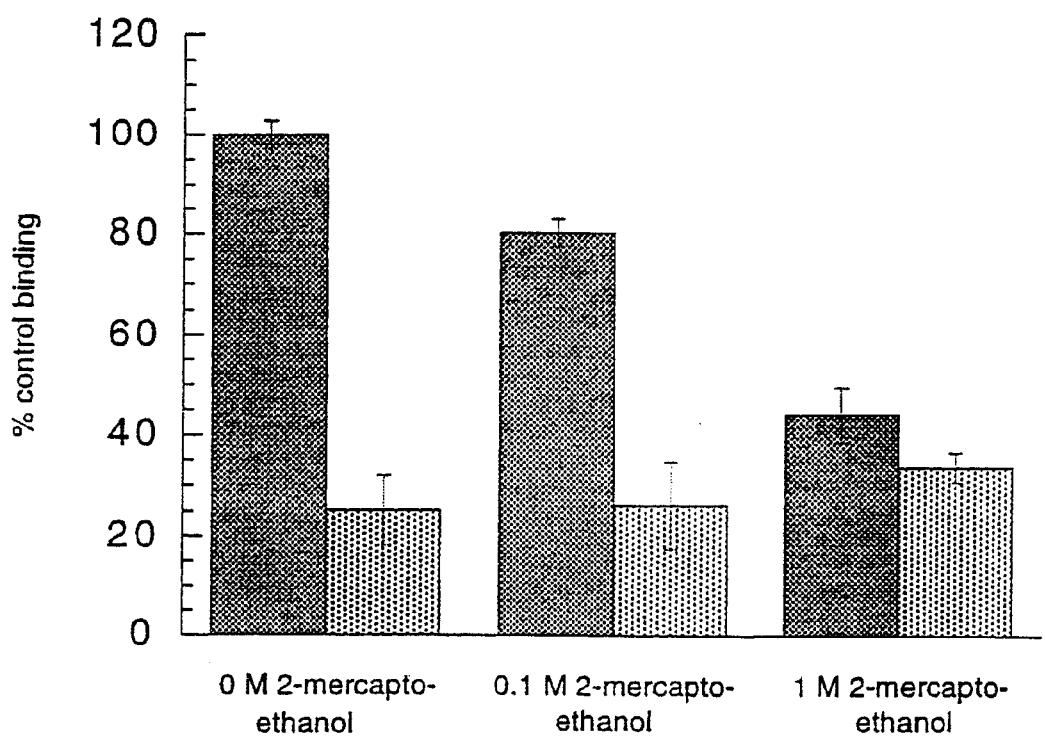
FIG. 10 is a graph of the effect of treatment of human leukocyte membranes with 2-mercaptoethanol on the binding of radioactively labelled underivatized, aqueous soluble β(1–3)-glucan to membranes. Solid columns indicate the saline control; stippled columns indicate underivatized, aqueous soluble β(1–3)-glucan sample.

Binding assays were carried out in the presence of 2-mercaptoethanol at the concentrations indicated in FIG. 10 (0, 0.1 and 1 M). Similar results were obtained when the same concentrations of dithiothreitol (DTT) were used. The high concentrations of reducing agents required to affect binding indicate the binding moiety does not contain an easily accessible disulfide bond that is essential for binding.

Figure 11:
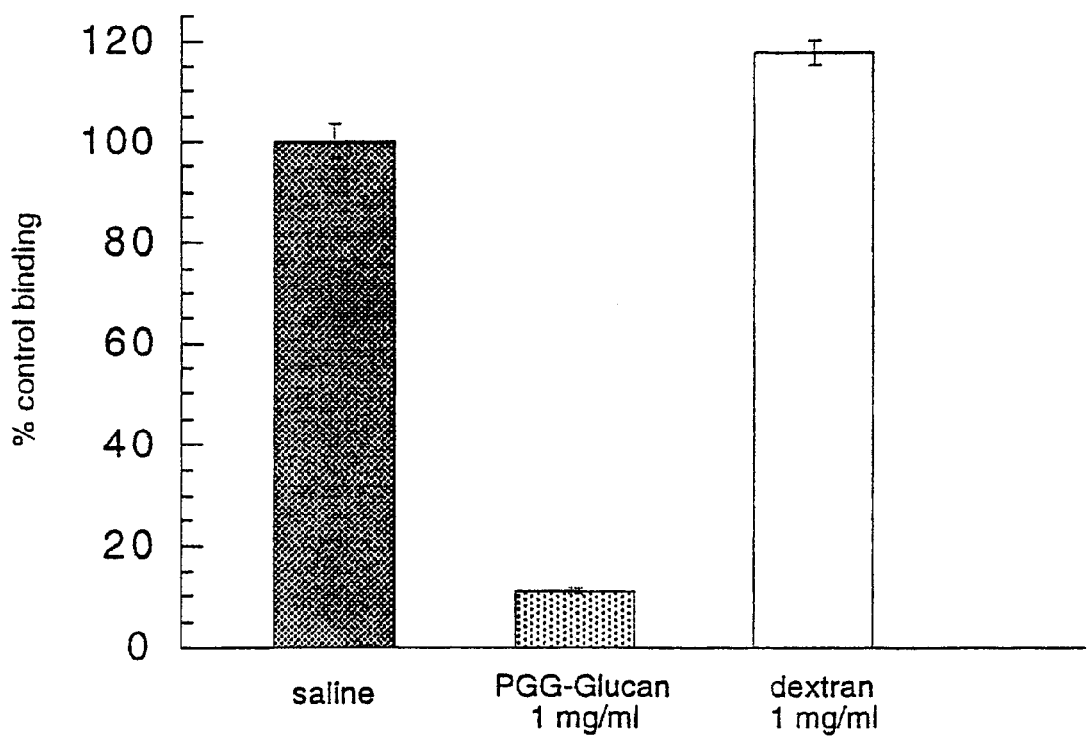
FIG. 11 is a graph of the effect on specific binding of chloroform/methanol/HBSS extraction of human leukocyte membranes.

Human leukocyte membranes were extracted with chloroform/methanol/HBSS (3:2:1) as described in the Examples. The protein-reduced fraction was used in a binding assay (non-oil/sucrose method) with the competitor indicated in FIG. 11, underivatized, aqueous soluble β(1–3)-glucan or dextran, at 1 mg/ml final concentration. These results (shown in FIG. 11) indicate that the binding moiety survives chloroform/methanol treatment.

Figure 12:
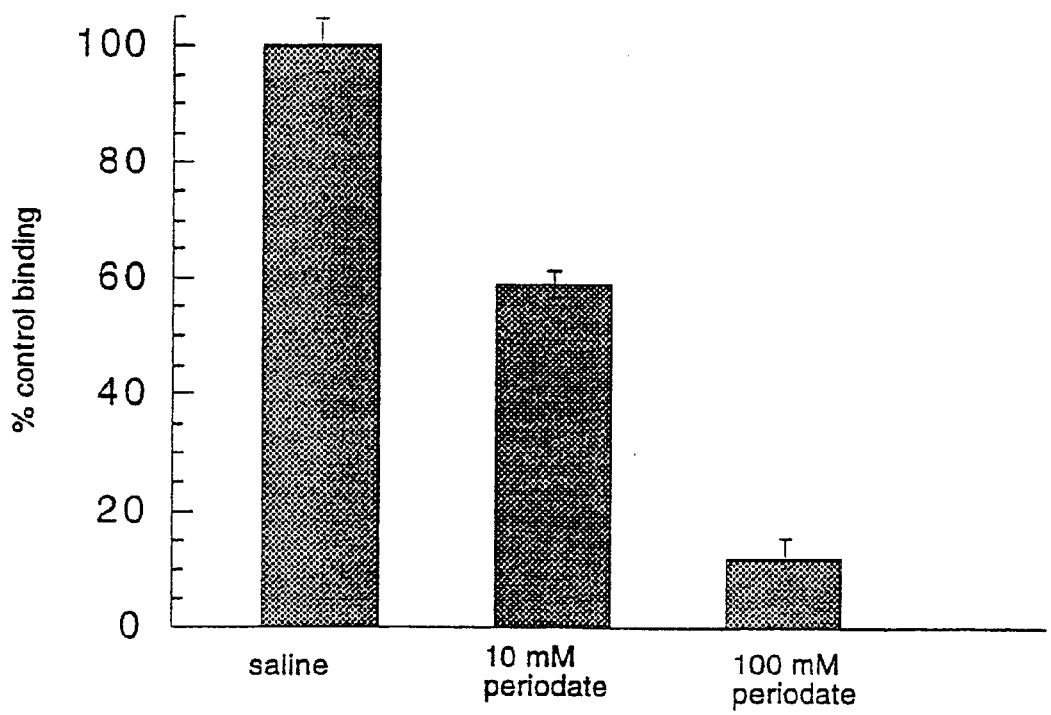
FIG. 12 is a graph of the effect of sodium periodate pretreatment of human leukocyte membranes on binding activity.
Figure 13:
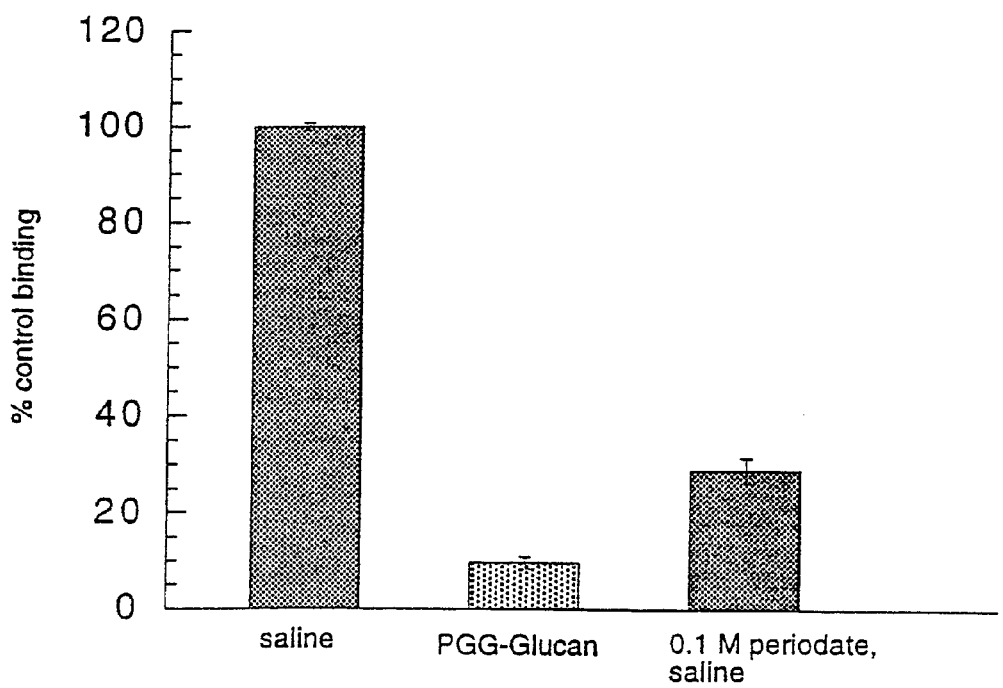
FIG. 13 is a graph of the effect of sodium periodate pretreatment of partially protein-depleted human leukocyte membranes on binding activity.

Human leukocyte membranes (500 µg protein) were incubated with sodium periodate at concentrations indicated in FIG. 12 (10 and 100 mM) for 30 minutes at room temperature, then centrifuged at 12,000×g for 10 minutes, rinsed and used in a binding assay (non-oil/sucrose; see FIG. 12). Protein-depleted membranes (derived from 1.87 mg human leukocyte membrane protein) were incubated in 0.1 M sodium periodate and treated as described above (FIG. 13).

The results show that the receptor is not affected by salt or low pH pretreatment of membranes and is enhanced by detergent pretreatment of membranes. The binding activity is decreased by sodium periodate treatment and by high concentrations of reducing agents. Furthermore, the binding site appears to be extractable with chloroform/methanol/water. Taken together, these data indicate that the binding site is not likely to be a peripheral protein and probably contains regions associated with the hydrophobic portion of the membranes. The effect of sodium periodate on binding indicates the membrane target for underivatized, aqueous soluble β(1–3)-glucan may be a glycoconjugate, consistent with the observation that the binding moiety survives chloroform/methanol treatment. The carbohydrate portion of the glycoconjugate may be associated with a protein, a lipid, or both, as glycoconjugate receptors which are glycolipids or glycoproteins are known in the art (Sandberg et al., *Infect. Immun.* 63(7):2625–2631 (1995)).

The distribution of the receptor for underivatized, aqueous soluble β(1–3)-glucan across various cell lines and human tissues was determined by assessing the binding of radioactively labeled underivatized, aqueous soluble β(1–3)-glucan to membranes derived from a variety of cell types (see Table 2). The amount of radioactively labeled underivatized, aqueous soluble β(1–3)-glucan binding is expressed as mean±standard deviation in ng/mg membrane protein. The non-specific binding is defined as radioactively labeled underivatized, aqueous soluble β(1–3)-glucan bound in the presence of greater than 100-fold excess unlabeled underivatized, aqueous soluble β(1–3)-glucan. The specific binding is determined by (Total Binding)–(Non-Specific Binding), with the number in parenthesis in Table 2 representing the percent total binding. Quantitation of complement receptor 3 (CR3) was carried out by flow cytometry using fluorescently-labeled anti-CD11b, and data are expressed as mean channel fluorescence (MCF) in arbitrary fluorescence units; background fluorescence for isotype controls were subtracted. The neutrophil sample was greater than 95 percent neutrophils by histology. The mononuclear cell sample was approximately 40–50 percent monocytes by histology.

The dominant cell type expressing receptors in human peripheral blood is the neutrophil, with mononuclear leukocytes (monocytes and lymphocytes) expressing less than 20% of the measured expression of neutrophils. The human monocytic cell line U937 does not bind detectable amounts of radioactively labeled underivatized, aqueous soluble β(1–3)-glucan, while the murine macrophage cell lines BMC2.3 (Dr. Kenneth Rock, Dana-Farber Cancer Institute, Boston, Mass.), RAW264.7 (ATCC) and P388D(1) (ATCC) express variable amounts of binding activity. When these three cell lines were assayed for CR3 expression by flow cytometry, the P388D(1) cells were found to be devoid of CR3. Thus, there was no correlation between radioactively labeled underivatized, aqueous soluble β(1–3)-glucan binding and CR3 expression. Consistent with this observation is the fact that CR3 is highly expressed in blood monocytes, which had little radioactively labeled underivatized, aqueous soluble β(1–3)-glucan binding activity. Finally, murine B and T cell lines (LP27.4 and DO11, respectively) did not bind radioactively labeled underivatized, aqueous soluble β(1–3)-glucan.

human leukocyte membranes was determined by incubating 2.2 mg/ml human leukocyte membranes with increasing concentrations of radioactively labeled underivatized, aqueous soluble β(1–3)-glucan in the presence (non-specific binding) or absence (total binding) of 50-fold excess unlabeled underivatized, aqueous soluble β(1–3)-glucan for 60 minutes at 37° C. Membrane-associated radioactivity was determined following centrifugation of the reaction mixture through a sucrose/oil density gradient as described in the Examples. Specific binding was calculated by subtracting non-specific binding from total binding. The data were fit by linear regression analysis to the equation $B=B_{max}(S/(S+Km))$, where B=radioactively labeled underivatized, aque-

TABLE 2

$^3$H-PGG-Glucan binding to various cell types

| Cell Type | Description | $^3$H-PGG-Glucan Bound (ng/mg protein) | | | CR3 (MCF) |
|---|---|---|---|---|---|
| | | Total | Non-Specific | Specific (%) | |
| neutrophil | human blood leukocyte | 16.0 ± 0.54 | 3.20 ± 0.30 | 12.8 (80) | — |
| mononuclear cells | human monocytes and lymphocytes | 2.80 ± 0.68 | 1.60 ± 0.52 | 1.2 (43) | — |
| U937 | human monocytic cell line | 0.34 ± 0.17 | 0.34 ± 0.02 | 0 | — |
| BMC2.3 | | 1.74 ± 0.06 | 0.85 ± 0.07 | 0.89 (51) | 542 |
| RAW264.7 | murine monocytic cell line | 1.70 ± 0.14 | 0.43 ± 0.06 | 1.27 (75) | 605 |
| P388D(1) | | 4.59 ± 0.53 | 1.94 ± 0.12 | 2.65 (58) | 26 |
| DO11 | murine monocytic cell line | 0.70 ± 0.30 | 0.7 ± 0.05 | 0 | — |
| LB27.4 | murine monocytic cell line murine T cell line murine B cell line | 1.10 ± 0.23 | 1.24 ± 0.01 | 0 | — |

Figure 3:
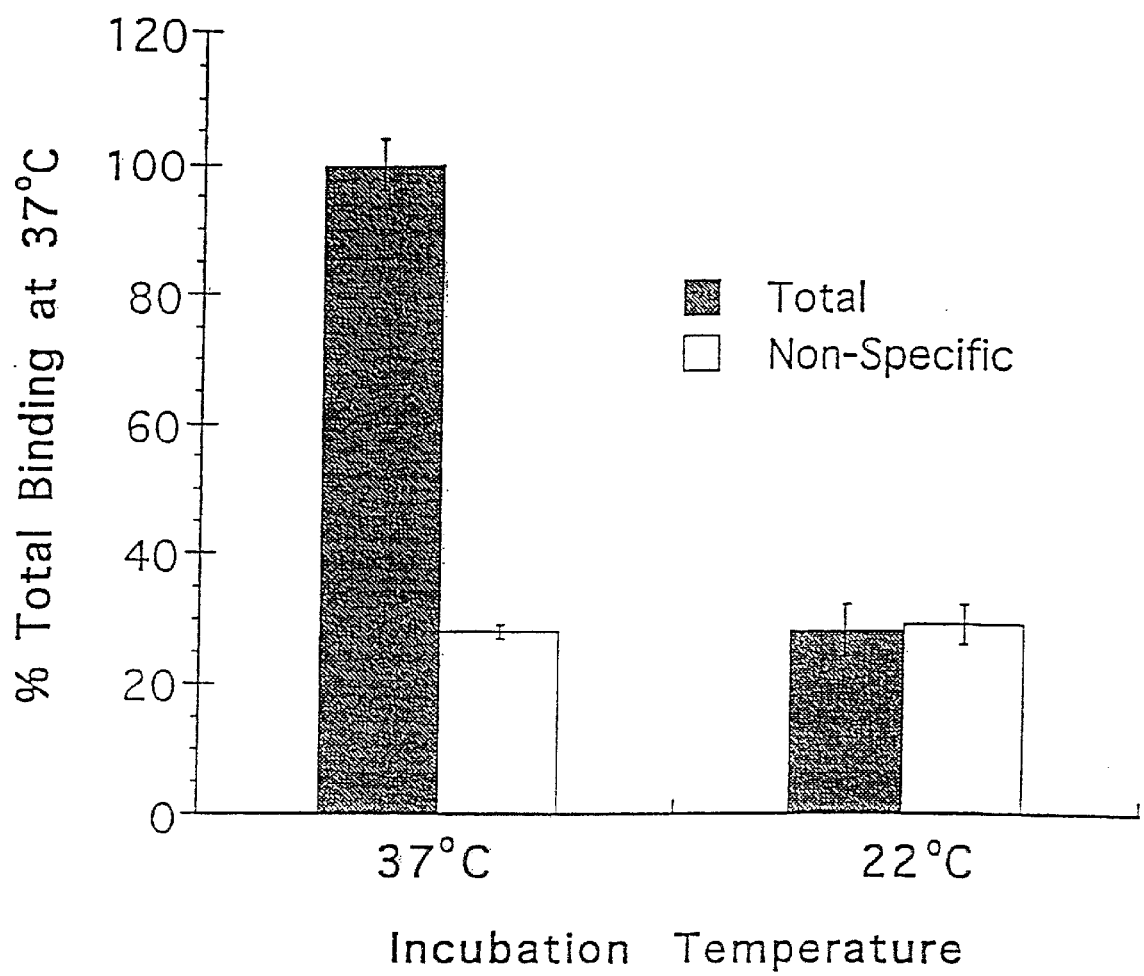
FIG. 3 is a graph of the effect of incubation temperature on the binding of radioactively labeled β(1–3)-glucan to human leukocyte membranes. Total binding is indicated by the shaded block, and non-specific binding is indicated by the open block. Data are expressed as a percent of the total binding at 37° C., and data points represent the mean±standard deviation of triplicate samples.

Incubation of radioactively labeled underivatized, aqueous soluble β(1–3)-glucan (1 μg/ml) with human leukocyte membranes (2 mg/ml) at either 37° C. or 22° C. for 60 minutes demonstrated a marked dependence on ambient temperature for binding to occur (FIG. 3). Similar results were obtained when the 22° C. incubation was extended to 4 hours or when the incubation was done at 4° C., while non-specific binding was not affected by temperature.

The binding activity of the radioactively labeled underivatized, aqueous soluble β(1–3)-glucan is sensitive to a β(1–3)-specific exoglucanase, indicating that the binding activity of the ligand is a β(1–3)-glucan. However, binding is not inhibited by either the anti-idiotype antibody of Czop (1990) or the anti-complement receptor 3 antibody (OKM1; Diamond et al., J. Cell Biol. 120:1031–1043 (1993)). This data, along with the lack of inhibition by aminated glucan, indicates that the receptor for underivatized, aqueous soluble β(1–3)-glucan is a novel leukocyte carbohydrate receptor.

Time course and concentration-dependence of radioactively labeled underivatized, aqueous soluble β(1–3)-glucan binding to human leukocyte membranes was determined by incubating 1 μg/ml of radioactively labeled underivatized, aqueous soluble β(1–3)-glucan with 2.5 mg/ml human leukocyte membranes in the presence or absence of unlabeled underivatized, aqueous soluble β(1–3)-glucan (1000 μg/ml) at 37° C. for various times. Bound radioactively labeled underivatized, aqueous soluble β(1–3)-glucan was separated from unbound ligand by centrifugation through a double layer density gradient, and the membrane pellet was solubilized and radioactivity determined. Equilibrium binding was achieved after 60 minutes at 37° C. at a concentration of 1 μg/ml radioactively labeled underivatized, aqueous soluble β(1–3)-glucan (FIG. 1).

Figure 2A:
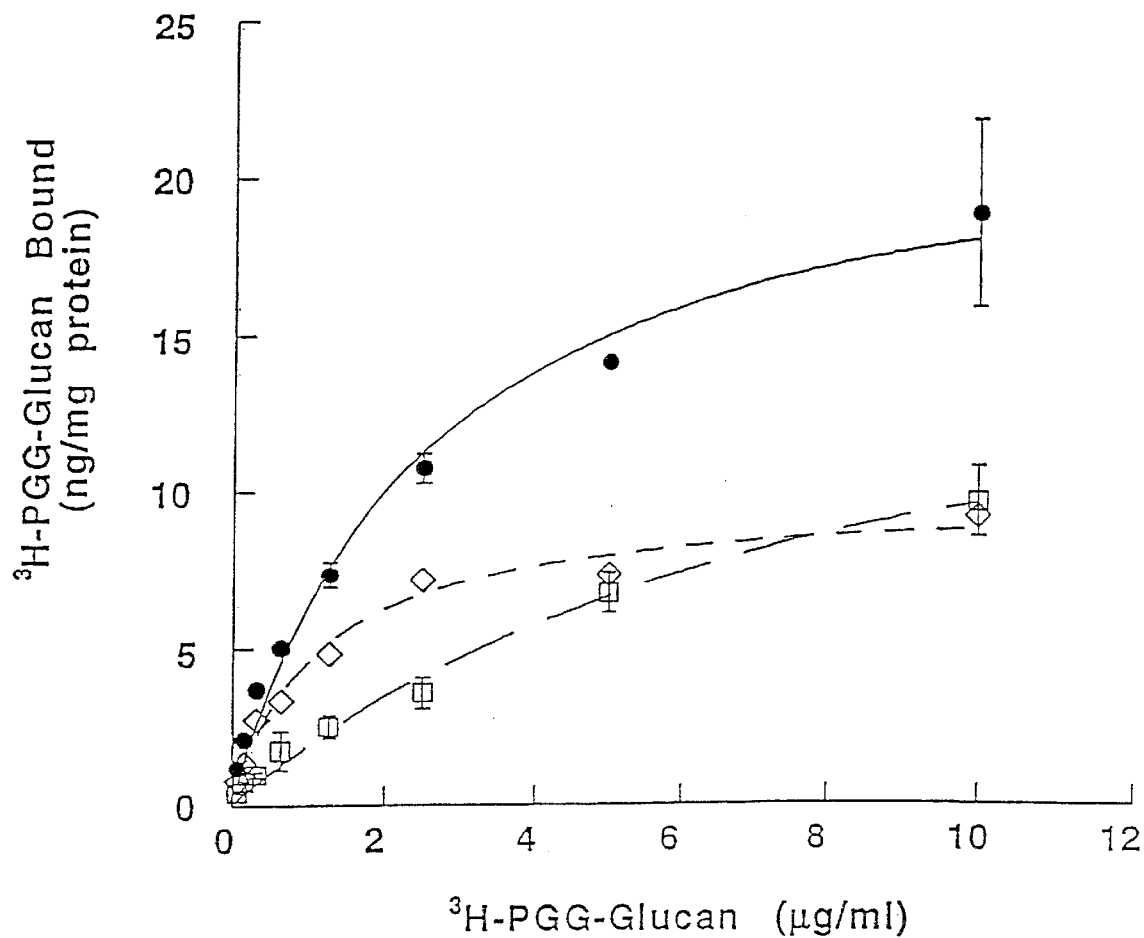
FIGS. 2A and 2B show a graphic illustration of concentration-dependence of radioactively labeled underivatized, aqueous soluble β(1–3)-glucan binding to human leukocyte membranes.
Figure 2B:
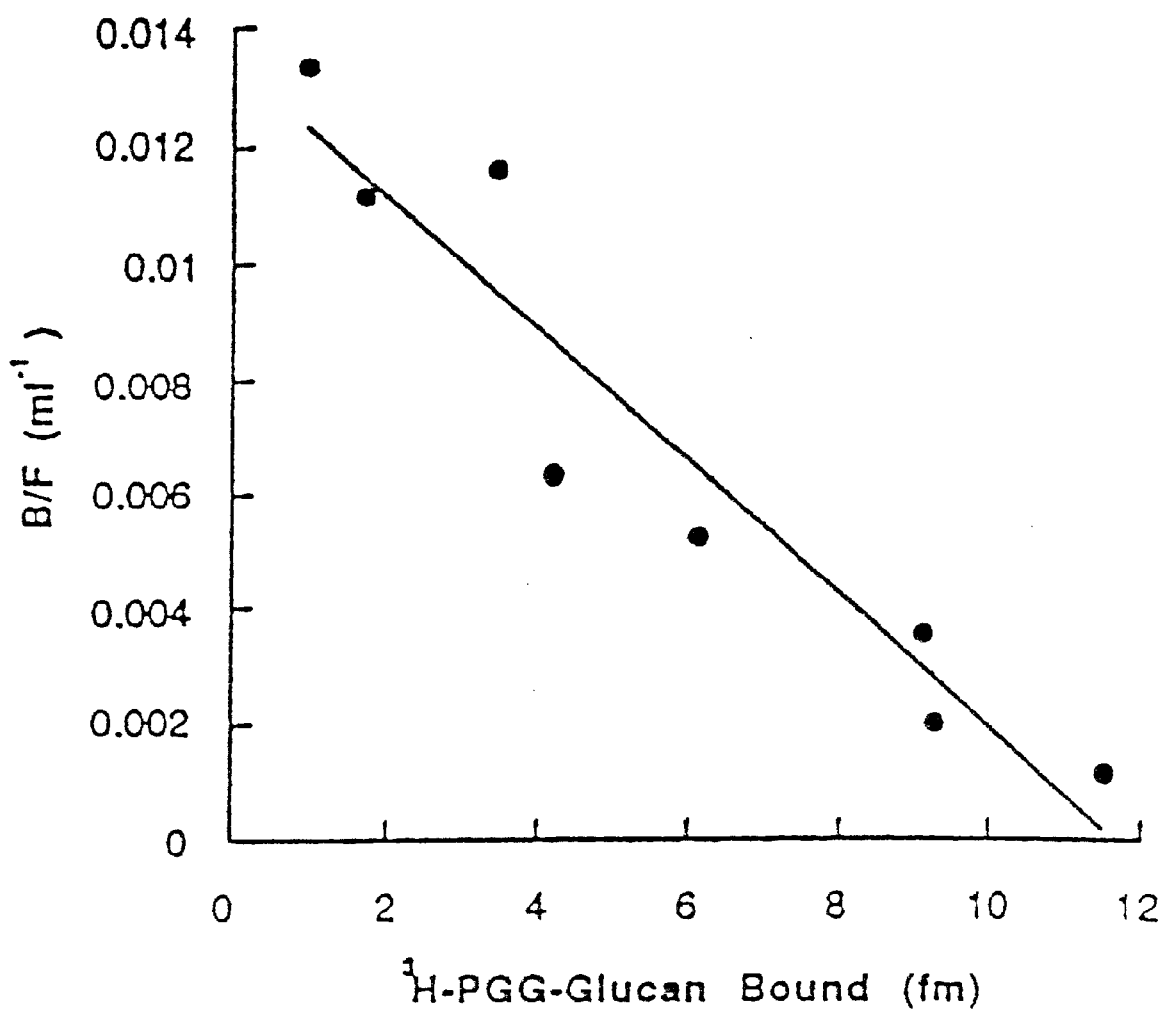

Concentration-dependence of radioactively labeled underivatized, aqueous soluble β(1–3)-glucan binding to ous soluble β(1–3)-glucan, $B_{max}$=maximal binding, S=radioactively labeled underivatized, aqueous soluble β(1–3)-glucan concentration and Km=concentration of radioactively labeled underivatized, aqueous soluble β(1–3)-glucan at half maximal binding. Saturation binding was achieved at a concentration of about 2.5 μg/ml (FIG. 2A). Scatchard analysis (FIG. 2B) yielded an apparent affinity of 1 nM and maximal binding of approximately 56 fm/mg protein, and the apparent dissociation constant is approximately 12 nM.

Figure 4:
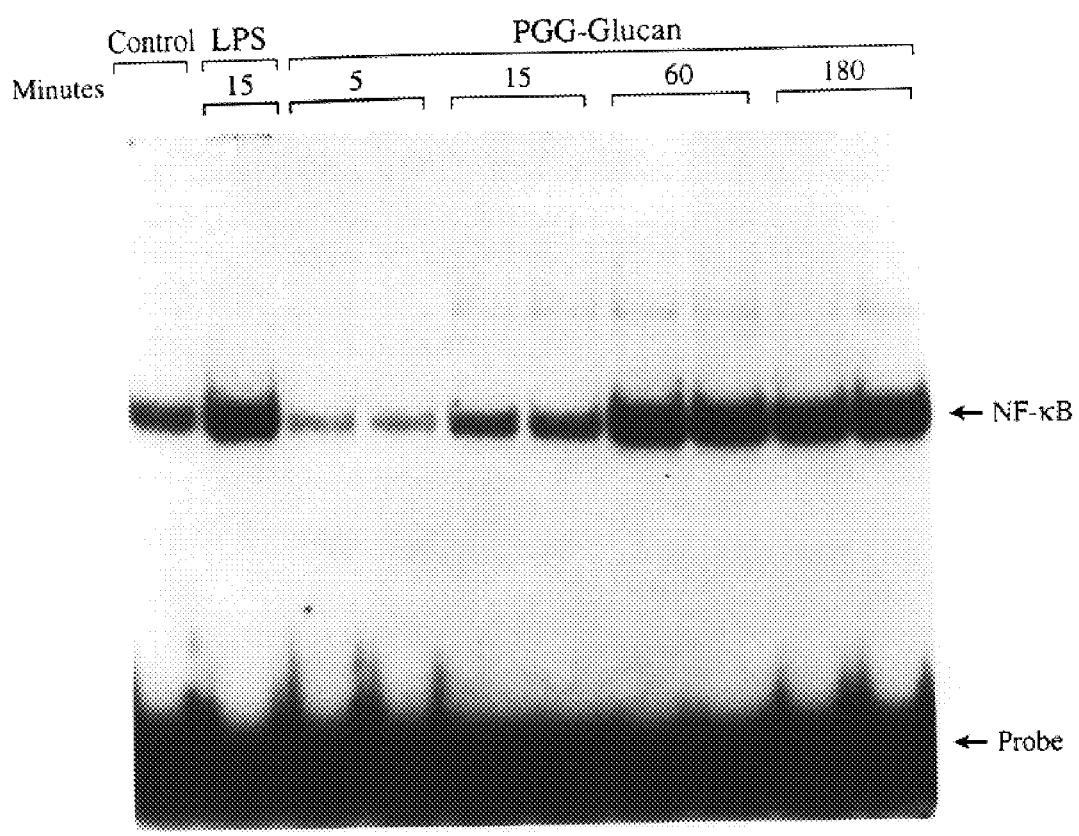
FIG. 4 is an autoradiograph of the time course for NF-κB activation by underivatized, aqueous soluble β(1–3)-glucan in the murine macrophage cell line BMC2.3, compared with a control and lipopolysaccharide. The lane for NF-κB is indicated with an arrow.
Figure 5:
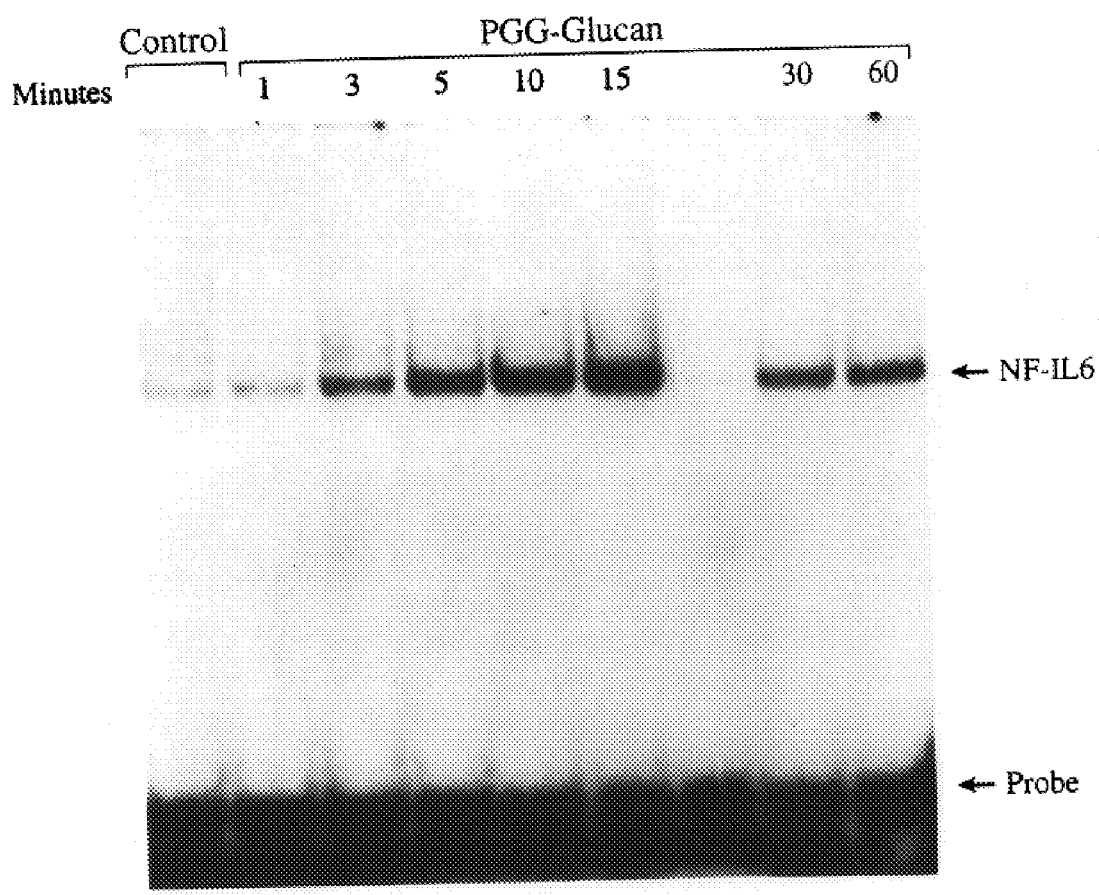
FIG. 5 is an autoradiograph of the time course of NF-IL6 activation by underivatized, aqueous soluble β(1–3)-glucan in the murine macrophage cell line BMC2.3 compared with control. The lane for NF-IL6 is indicated with an arrow.

In order to assess the activation of signal transduction as exemplified by the modulation of one or more transcriptional regulatory factors by underivatized, aqueous soluble β(1–3)-glucan, BMC2.3 cells were incubated with 3 μg/ml underivatized, aqueous soluble β(1–3)-glucan for various periods of time at 37° C. Nuclear extracts were prepared and incubated with $^{32}$P-labeled DNA oligonucleotides specific for NF-κB or NF-IL6. The protein-$^{32}$P DNA complexes were separated from unbound $^{32}$P DNA by gel electrophoresis (electrophoretic mobility shift assay, EMSA). The results (FIGS. 4 and 5) show a time dependent increase in protein-DNA complexes, indicating that these transcription factors were activated by underivatized, aqueous soluble β(1–3)-glucan. Inhibition of the formation of this complex by unlabeled DNA probe, and lack of inhibition by mutant probe, demonstrate the specificity of this interaction (data not shown).

Figure 16A:
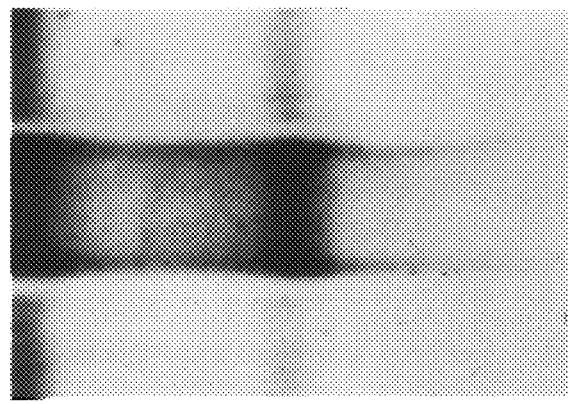
FIGS. 16A and 16B are photographs showing that underivatized, aqueous soluble β(1–3)-glucan activates the nuclear transcription factors NF-kB and NF-IL6 in human neutrophils.
Figure 16B:
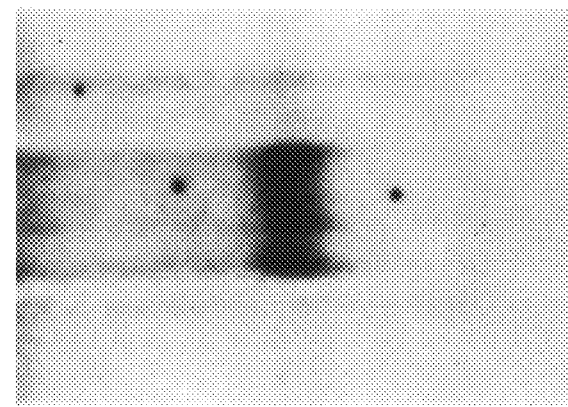

Purified human neutrophils were incubated with or without underivatized, aqueous soluble β(1–3)-glucan (3 μg/ml) or dextran (3 μg/ml) for 60 minutes at 37° C. Nuclear extracts were prepared and protein/DNA complex formation assessed by electrophoretic mobility shift assay (EMSA). As shown in FIGS. 16A and 16B, underivatized, aqueous soluble β(1–3)-glucan increased the binding of nuclear extract proteins to an NF-kB or NF-IL6 specific 32P-labeled oligonucleotide probe relative to extracts from either control or dextran-treated neutrophils.

Although receptors for both soluble and particulate β-glucans have previously been described, the characterization of the binding interaction between underivatized, aqueous soluble β(1–3)-glucan and its receptor on human leukocyte membranes indicates that the β-glucan receptor described herein is a distinct molecular entity from previously described receptors.

The particulate β-glucan receptor described by Czop (1990) is found on human monocytes and U937 cells. Underivatized, aqueous soluble β(1–3)-glucan binding is nominal on monocytes relative to peripheral polymorphonuclearcytes (PMN), and no binding was found on U937 cells. Furthermore, the anti-idiotype antibody generated by Czop (1990), which presumably occupies the glucan binding site, effectively inhibits glucan particle phagocytosis in monocytes but is ineffective in inhibiting underivatized, aqueous soluble β(1–3)-glucan binding.

The receptor for aminated glucan present on murine peritoneal macrophages (Konopski et al., (1994)) binds to their described aminated glucan at 4° C., whereas underivatized, aqueous soluble β(1–3)-glucan does not bind to its receptor at room temperature or below. In addition, samples of soluble aminated glucan did not compete for binding to the receptor for underivatized, aqueous soluble β(1–3)-glucan (Table 1).

The β-glucan binding activity of CR3 as described by Thornton et al. (1996) is inhibited by monoclonal antibodies directed to the I-domain of CR3. One of these antibodies was OKM1, which inhibited glucan binding in the previously described system, but had no inhibitory effect on underivatized, aqueous soluble β(1–3)-glucan binding. Human peripheral blood PMN had five to ten-fold more specific underivatized, aqueous soluble β(1–3)-glucan binding relative to mononuclear cells, but both PMN and monocytes are known to express high levels of CR3.

More recently, a receptor for a phosphorylated derivative of β-glucan expressed at extremely high levels in U937 cells was described (Muller et al., *J. Immunol.* 156:3418–3425 (1996)). Again, no underivatized, aqueous soluble β(1–3)-glucan binding was observed in U937 membranes.

Particulate β-glucan receptors described by Goldman et al. (*Exp. Cell. Res.* 174(2):481–490 (1988)) can be inhibited by soluble glucans in the size range of 2,000–4,000 daltons, while underivatized, aqueous soluble β(1–3)-glucan binding is not inhibited by laminarin (molecular weight of approximately 5,000 daltons), or a single chain conformer of β-glucan of molecular weight 18,000 daltons. The receptor of Goldman et al. is expressed only following induction with retinoic acid or 1α,25-hydroxyvitamin D3 (Goldman, *Immunology* 63(2):319–324 (1988)), whereas underivatized, aqueous soluble β(1–3)-glucan binds to uninduced P388D (1) cells. Phagocytosis of glucan particles by salmon macrophages can be inhibited almost completely by high concentrations (800 μM) of laminariheptose (Engstad and Robertsen (1994)), which had no effect on underivatized, aqueous soluble β(1–3)-glucan binding (data not shown).

As described herein, several glycosphingolipids immobilized on a polystyrene 96-well plate exhibited significant specific binding to $^3$H-underivatized, aqueous soluble β(1–3)-glucan, including lactosyl ceramide (LacCer) (from various sources), galactosyl ceramides (GalCer), globotriaosyl ceramide, and asialoganglioside-GM1 (see Table 3). These compounds have in common a terminal galactose, which may therefore be involved in binding interactions between $^3$H-underivatized, aqueous soluble β(1–3)-glucan and the glycosphingolipid. A terminal galactose alone is not sufficient for binding, however, since psychosine (1-galactosyl sphingosine) does not show appreciable binding. This compound lacks the fatty acid portion of ceramide.

While several fatty acid structures in LacCer can support binding of $^3$H-underivatized, aqueous soluble glucan, as shown with HPLC fractionated LacCer from HLM in Table 4, the carbon-carbon double bond found in C18:1 sphingosine is apparently important for binding, since the commercially available dihydro-sphingosine LacCers do not bind.

The binding of $^3$H-underivatized, aqueous soluble β(1–3)-glucan to LacCer was also found to be temperature dependent, similar to that with HLM. Binding occurs at 37° C., but not at 4° C., as indicated in Table 5. The temperature specificity was seen with two different sources of LacCer.

Figure 14:
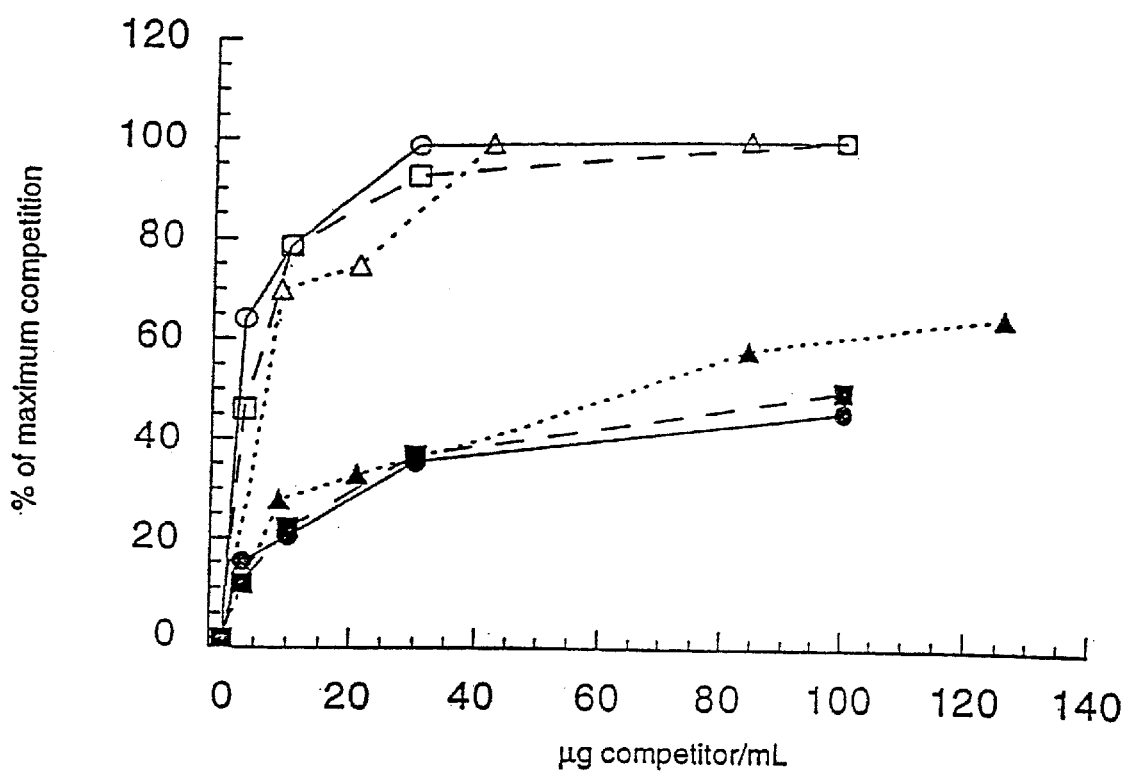
FIG. 14 is a graph of the comparison of underivatized, aqueous soluble β(1–3)-glucan and single helix competition of $^3$H-underivatized, aqueous soluble β(1–3)-glucan binding in three assay formats. Underivatized, aqueous soluble β(1–3)-glucan or single helix glucan was used at designated concentrations to compete for $^3$H-underivatized, aqueous soluble β(1–3)-glucan binding to lactosyl ceramide (LacCer) in a 96-well plate (triangles), or to lactosyl ceramide in reconstituted membranes (squares), or to human leukocyte membranes (circles). Open symbols represent underivatized, aqueous soluble β(1–3) glucan, and closed symbols represent single helix. Maximum competition was assigned at the highest concentration of underivatized, aqueous soluble β(1–3)-glucan used as competitor in each type of assay.
Figure 15:
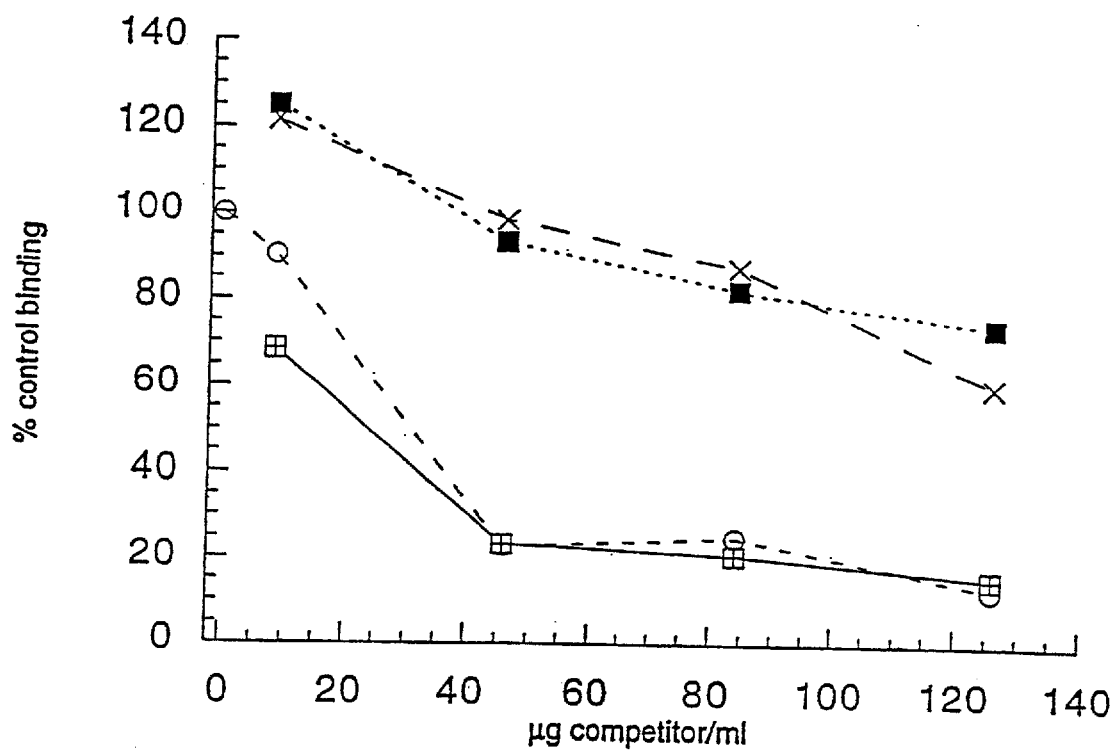
FIG. 15 is a graphic illustration of data showing that underivatized, aqueous soluble β(1–3) glucan and high molecular weight underivatized, aqueous soluble β(1–3) glucan (Network) compete more effectively for $^3$H-underivatized, aqueous soluble β(1–3)-glucan binding to lactosyl ceramide in a 96-well plate assay than do single helix or laminarin. Underivatized, aqueous soluble β(1–3) glucan (circles), single helix (closed squares), laminarin (crosses) and high molecular weight underivatized, aqueous soluble β(1–3)-glucan (Network) (hatched squares) were used at designated concentrations to compete for $^3$H-underivatized, aqueous soluble β(1–3) glucan binding to lactosyl ceramide (bovine) in a 96-well plate assay. "% control binding" means the percent of binding with no competitor.

The conformer specificity of competition for $^3$H-underivatized, aqueous soluble β(1–3)-glucan binding was also similar to that previously described with HLM. As shown in FIG. 14, underivatized, aqueous soluble β(1–3)-glucan competes for $^3$H-underivatized, aqueous soluble β(1–3)-glucan binding to HLM, and to LacCer in both the 96-well assay and the reconstitution assay to the same degree. In contrast, single helix (SH)glucan does not compete efficiently in any of the assays. Also, Network, a glucan preparation comprising glucan that is primarily in the triple helix conformation and has a molecular weight of greater than one million, competes similarly to underivatized, aqueous soluble β(1–3)-glucan, while laminarin does not compete efficiently for $^3$H-underivatized, aqueous soluble β(1–3)-glucan binding to LacCer in the 96-well plate assay (see FIG. 15).

TABLE 3

Specific Binding of $^3$H-underivatized, Aqueous Soluble β(1–3)-glucan (PGG-Glucan) to various sphingolipids in the 96-well plate assay

| Sphingolipid | 3H-PGG-Glucan Bound (ng/μg sphingolipid) |
| --- | --- |
| LacCer (HLM) | 3.14 ± 0.29 |
| LacCer (bovine) | 2.18 ± 0.39 |
| LacCer (porcine) | 2.35 ± 0.23 |
| GalCer I | 1.02 ± 0.32 |
| GalCer II | 3.90 ± 0.14 |
| Ceramides | 0.02 ± 0.01 |
| Sulfatides | 0.00 ± 0.01 |
| Sphingosine | 0.02 ± 0.00 |
| Psychosine | 0.09 ± 0.00 |
| Asialoganglioside-GM2 | 0.00 ± 0.01 |
| Globoside | 0.00 ± 0.01 |
| GlobotriaosylCer | 0.84 ± 0.13 |
| Glucocerebrosides (GlcCer) | 0.12 ± 0.03 |
| Asialoganlioside-GM1 | 0.50 ± 0.10 |

TABLE 4

Specific binding of $^3$H-underivatized, aqueous soluble β(1–3)-glucan (PGG-Glucan) to LacCer of defined structures in the 96-well plate assay

| | Fatty Acid | Long Chain Base | $^3$H-PGG-Glucan bound |
| --- | --- | --- | --- |
| LacCer (HLM) | C16:0 | C18:1 | 3.31 |
| | C18:0 | C18:1 | 1.93 |
| | C24:2 | C18:1 | 2.01 |
| | C24:1 | C18:1 | 2.31 |
| | C22:0 | C18:1 | 3.57 |
| | C24:0 | C18:1 | 3.14 |
| N-Palmitoyl-DL-dihydrolacto-cerebroside | C16:0 | C18:0 | 0.00 |
| N-Stearoyl-DL-dihydrolacto-cerebroside | C18:0 | C18:0 | 0.00 |
| N-Lignoceroyl-DL-dihydrolacto-cerebroside | C24:0 | C18:0 | 0.00 |

TABLE 5

Temperature dependence of $^3$H-underivatized, aqueous soluble β(1–3)-glucan (PGG-Glucan) specific binding to lactosyl ceramides

|  | Temperature | $^3$H-PGG-Glucan bound (ng/µg LacCer) |
|---|---|---|
| LacCer (HLM) | 37° C. | 1.76 |
|  | 4° C. | 0.00 |
| LacCer (bovine) | 37° C. | 2.50 |
|  | 4° C. | 0.01 |

TABLE 6

Competition of $^3$H-underivatized, aqueous soluble β(1–3)-glucan (PGG-Glucan) binding to GalCer II

| Ligand | Concentration (mg hexose/mL) | % control binding |
|---|---|---|
| none | — | 100 |
| PGG-glucan | 0.01 | 23.6 |
|  | 0.1 | 3.0 |
|  | 1.0 | 1.4 |
| SH | 0.01 | 46.1 |
|  | 0.1 | 10.7 |

From the results described above, it appears that an in vivo receptor for underivatized, aqueous soluble β(1–3)-glucan is LacCer. However, other compounds tested as described above also have an affinity for underivatized, aqueous soluble β(1–3)-glucan; these compounds are intended to be encompassed by the term "receptor" as described herein. For example, these compounds can be used in place of the LacCer receptor in the assays described herein. From this work, it appears that there are three characteristics which determine the affinity of a compound for underivatized, aqueous soluble β(1–3)-glucan: length of the fatty acid chain of the compound, presence of a terminal galactose in the compound, and presence or absence of a double bond in the sphingosine portion of the compound. Specifically, compounds shown herein to have an affinity for underivatized, aqueous soluble β(1–3)-glucan, have a fatty acid chain of from about 16 to about 24 carbons in length, contain a terminal galactose, and contain a double bond in the sphingosine portion. However, compounds having fatty acid chains of less than 16 and greater than 24 carbons are also contemplated by the invention. Furthermore, as used herein, "terminal galactose" is intended to encompass unmodified galactose as well as derivatized or modified galactose, such as sulphonated galactose. Accordingly, compounds having these characteristics are included in the present invention and are suitable for use in the methods described herein, along with other compounds having an affinity for underivatized, aqueous soluble β(1–3)-glucan.

As a result of the work described herein, it is possible to monitor the underivatized, aqueous soluble β(1–3)-glucan manufacturing process and characterize the product. That is, test samples can be included in a standard competition receptor binding assay to allow characterization of the molecule in terms of relative affinity for the receptor. This characterization will yield information with respect to some or all of the following characteristics: batch to batch quality, identification of product as a β(1,3)-glucan of a particular conformation and purity of the product.

As a further result of the work described herein, it is possible to use the receptor for underivatized, aqueous soluble β(1–3)-glucan to measure β-glucans in fluids. Test samples can be included in standard capture or competition assays and compared to a standard curve generated with a known β-glucan standard. This method can be used to measure soluble β-glucans in serum, plasma, urine, synovial fluid, cerebrospinal fluid, lung lavage, bile and other bodily fluids, as a diagnostic for fungemia. It can also be used to measure β-glucan levels in food manufacturing processes to test for fungal contamination, as well as to monitor yeast fermentation.

Test samples can also be included in standard capture or competition assays and compared with a standard sample to elucidate structure-activity relationships. Alternatively, the test sample binding can be tested directly after radiolabeling. Samples can also be tested in an underivatized, aqueous soluble β(1–3)-glucan receptor-mediated assay to test for inhibition or stimulation of these functions. For example, such assays can be used in the development of polymer or small molecule receptor agonists or to develop a receptor antagonist to inhibit an inappropriate immunoenhancement, such as to prevent a transplant rejection which might occur as a result of an opportunistic fungal infection during immunosuppressive therapy.

The discoveries disclosed herein can also be used to target delivery of various agents to receptor-positive cells. For example, various agents can be conjugated (e.g., chemically conjugated, cross-linked or covalently bonded) to underivatized, aqueous soluble β(1–3)-glucan to produce a conjugate molecule which can be targeted to receptor-positive cells such as PMN and macrophages. Such a targeted delivery system can be used to enhance the delivery of agents such as antimicrobials for resistant intracellular pathogens (e.g., mycobacterium, leishmania, malaria), cytotoxins for receptor-positive leukemias, genes for gene therapy (e.g., for enhanced cytokine production or replacement for dysfunctional enzymes), or antigens for enhanced presentation and production of specific antibodies or T-cell activation.

The binding specificity of the underivatized, aqueous soluble β(1–3)-glucan to its receptor provides a method for purification of both receptor-positive and receptor-negative cells (i.e., cells which do not contain the receptor); for example, underivatized, aqueous soluble β(1–3)-glucan can be affixed to a solid matrix and used as an affinity matrix to positively select receptor-positive cells or to negatively select receptor-negative cells. Similarly, anti-receptor antibodies can be used in place of the immobilized underivatized, aqueous soluble β(1–3)-glucan. Cells which are purified by this method can subsequently be expanded for use in cell therapy.

Furthermore, the present invention makes possible the generation of anti-receptor antibodies for diagnostic purposes. Monoclonal or polyclonal antibodies can be produced using enriched or purified receptor preparations by standard techniques. Thus, the present invention also relates to antibodies which bind the receptor for underivatized, aqueous soluble β(1–3)-glucan. For instance, polyclonal and monoclonal antibodies which bind to the described receptor are within the scope of the invention. A mammal, such as a mouse, hamster or rabbit, can be immunized with an immunogenic form of the receptor (i.e., an antigenic portion of the receptor which is capable of eliciting an antibody response). Techniques for conferring immunogenicity include, for example, conjugation to carriers or other techniques well known in the art. The antigen can be administered in the presence of an adjuvant, and the progress of immunization can be monitored by detection of antibody titers in plasma or serum. Standard ELISA or other immunoassays can be used with the immunogen as antigen to assess the levels of antibody. Antibodies to the glycolipid receptor described herein can be produced by standard techniques such as, for example, those described in Koscielak et al. (*Immunochemistry* 5:441 (1968)), Hakomori (*Methods of Enzymol.* 28:232–236 (1972)) and Marcus and Janis (*J.*

*Immunol.* 104:1530 (1970)). Such antibodies can be used to identify alterations in receptor-positive or receptor-negative cell populations which reflect disease pathology (e.g., response to cryptic fungal infection or leukemia).

This invention also pertains to a method of altering (e.g., activating or deactivating) signal transduction pathways, for example through modulation of transcriptional regulatory factors in receptor-positive cells, i.e., cells which contain the receptor for underivatized, aqueous soluble β(1–3)-glucan. In one embodiment of the invention, the transcriptional regulatory factor is from the NF-κB and/or NF-IL6 and/or jun/fos families of transcriptional regulatory factors. For example, the transcription factor can be NF-κB, NF-IL6 or AP-1.

According to the method of the present invention, the activity of the receptor for underivatized, aqueous soluble β(1–3)-glucan is activated through binding of an underivatized, aqueous soluble β(1–3)-glucan, whereby a signal transduction pathway which is regulated by a transcriptional regulatory factor (e.g., from the NF-κB, NF-IL6 or jun/fos families) is activated. Activation of the receptor can comprise, among others, an alteration in the receptor conformation, formation of a ligand-receptor complex, or alteration of the ligand-receptor complex.

Alternatively, the activity of the receptor can be activated by an agent which mimics the binding and activation ability of an underivatized, aqueous soluble β(1–3)-glucan. In a particular embodiment, the transcriptional regulatory factor is activated as a result of ligand binding. In another embodiment, the activity of the transcriptional regulatory factor is decreased, either partially or totally, by the binding of an agent which binds the receptor (and thus excludes the underivatized, aqueous soluble β(1–3)-glucan), but lacks the ability to activate the receptor.

Other signal transduction pathways which can be altered by the methods of the present invention include the ras/raf-1/MAP kinase pathway, the G-protein/phospholipase C/protein kinase C. pathway, the JAK/STAT pathway, the phospholipase A pathway, G-protein/phospholipase D/phosphatidic acid pathway and the c-AMP-dependent pathway. In each pathway, an appropriate activator or indicator of the signal pathway is activated by binding of underivatized, aqueous soluble β(1–3)-glucan to its receptor, and modulation of this binding can alter the corresponding signal transduction.

The present invention also pertains to a novel assay for identifying agents which alter the effect of underivatized, aqueous soluble β(1–3)-glucan on signal transduction pathways such as activation of transcriptional regulatory factors. This assay comprises combining underivatized, aqueous soluble β(1–3)-glucan, the receptor for underivatized, aqueous soluble β(1–3)-glucan and an agent to be tested under conditions in which binding of underivatized, aqueous soluble β(1–3)-glucan to its receptor occurs (i.e., conditions suitable for binding of underivatized, aqueous soluble β(1–3)-glucan to the receptor for underivatized, aqueous soluble β(1–3)-glucan). Binding of underivatized, aqueous soluble β(1–3)-glucan to its receptor activates the receptor, which in turn activates a signal transduction pathway as shown by transcriptional regulatory factors such as those of the NF-κB and/or NF-IL6 and/or jun/fos families. The extent of activation of the selected transcriptional regulatory factor in the presence of an agent to be tested is determined (e.g., using radiolabeled DNA oligonucleotides specific for the transcriptional regulatory factor, as in the Examples) and compared with the extent of activation of the selected transcriptional regulatory factor in the absence of the agent to be tested; a difference in the extent of activation indicates that the agent alters the effect of underivatized, aqueous soluble β(1–3)-glucan on activation of the transcriptional regulatory factor. An increase in the activation of the transcriptional regulatory factor in the presence of the agent indicates that the agent enhances, i.e., prolongs or increases, the activation. A decrease in the activation of the transcriptional regulatory factor in the presence of the agent indicates that the agent diminishes, i.e., shortens or decreases, the activation.

The invention also pertains to an assay or method for assessing the specificity of an interaction between a carbohydrate and a glycolipid. According to the method, a selected carbohydrate and a selected glycolipid are combined under conditions suitable for interaction between the carbohydrate and glycolipid, and the extent of interaction between the carbohydrate and glycolipid is determined. This extent of interaction is compared with the extent of interaction between the selected glycolipid and selected carbohydrate in the presence of another glycolipid or carbohydrate.

For example, to determine the affinity of a particular glycolipid for a selected carbohydrate, the two are combined under appropriate conditions, and the extent of interaction is determined. Typically, the interaction will be binding. The extent of interaction is then compared with the extent of interaction in the presence of a selected competitor carbohydrate. In this way, the specificity of the interaction between the glycolipid and the selected carbohydrate can be compared with the interaction between the glycolipid and a competitor carbohydrate, and the relative specificities can be determined.

Similarly, to determine the affinity of a particular carbohydrate for a selected glycolipid, the two are combined under appropriate conditions, and the extent of interaction is determined. The extent of interaction is then compared with the extent of interaction in the presence of a selected competitor glycolipid. In this way, the specificity of the interaction between the carbohydrate and the selected glycolipid can be compared with the interaction between the carbohydrate and a competitor glycolipid, and the relative specificities can be determined. In a particular embodiment of the invention, the glycolipid is LacCer. In another embodiment of the invention, the carbohydrate is underivatized, aqueous soluble β(1–3)-glucan.

The following Examples are offered for the purpose of illustrating the present invention and are not to be construed to limit the scope of this invention. The teachings of all references cited herein are hereby incorporated herein by reference.

EXAMPLES

Materials

Lactosyl ceramide (HLM) was purified from human leukocyte membranes as described below. All other sphingolipids, ceramides, and phospholipids were from Sigma Chemical Co. (St. Louis, Mo.), except lactosyl ceramide (porcine) which was from Matreya, Inc. (Pleasant Gap, Pa.). SOLVABLE™ was from DuPont, NEN (Boston, Mass.). 96-well polystyrene plates were from Corning (New York).

Preparation of Radioactively Labeled Underivatized, Aqueous Soluble β(1–3)-Glucan Underivatized, aqueous soluble β(1–3)-glucan (PGG-glucan, 17 mg; HPD0144, Alpha-Beta Technology, Worcester, Mass.) was incubated with $NaIO_4$ (225 mg; Sigma, St. Louis, Mo.) in sterile pyrogen-free (SPF) water for 72 hours at room temperature. The periodate was quenched by the addition of 50 mg glycerol. The underivatized, aqueous soluble β(1–3)-glucan was dialyzed against SPF water, and then reductively labeled with 100 mCi of $NaB^3H_4$ (New England Nuclear, Boston, Mass.). Radioactively labeled underivatized, aqueous soluble β(1–3)-glucan was separated from tritiated low molecular weight by-products by dialysis (10 K cut-off) and ultrafiltration. Purity of the labeled product was assessed by gel permeation chromatography.

Preparation of Human Neutrophils

Fresh whole blood was obtained from normal human volunteers using acid citrate dextrose as an anticoagulant. Following dextran sedimentation, cells were centrifuged (400×g, 7 minutes) and resuspended in autologous plasma. Cells were then layered over a Ficoll gradient (Lymphocyte Separation Medium; Organon Teknika, Durham, N.C.) and centrifuged (400×g, 30 minutes). Cells recovered from the pellet were hypotonically lysed to remove residual RBC. The remaining cells were greater than 95% neutrophils as judged by morphological criteria.

Preparation of Human Leukocyte Membranes

Buffy coat cells from human donors (Red Cross, Dedham, Mass.) were incubated in 3% dextran for 15–20 minutes at room temperature to separate leukocytes from red cells. The leukocyte-rich supernatant was pelleted (500×g, 7 minutes) and washed once in ice cold phosphate buffered saline (PBS; Life Technologies, Grand Island, N.Y.). All subsequent operations were performed at 4° C. The remaining red cells were removed by hypotonic lysis, and the leukocytes recovered by centrifugation (850×g, 7 minutes). The cell pellet was resuspended in approximately 3–4×volume PBS, and protease inhibitors were added (5 mM EDTA, 40 $\mu$g/ml aprotinin, 1 $\mu$M pepstatin A, 1 $\mu$g/ml leupeptin, 50 $\mu$M PMSF). The cells were disrupted by probe sonication (50 watts, 30×1 second pulses). Disruption of cells was monitored microscopically. Nuclei and remaining intact cells were removed by low speed centrifugation (700×g, 7 minutes). Occasionally, the low speed pellet was resonicated and subjected to another low speed centrifugation. The low speed supernatants were then collected by high speed ultracentrifugation (180,000×g, for 1 hour). Membrane pellets were resuspended in Hanks' balanced salt solution containing $Ca^{++}$ and $Mg^{++}$ (HBSS). Membrane protein was determined using the BCA or Comassie method (Pierce, Rockland, Ill.). Bovine serum albumin (Sigma, St. Louis, Mo.) was added to 1 mg/ml from a 10×stock, and the membranes stored in liquid nitrogen at 4–5 mg/ml. In some cases membranes were stored frozen without added protein; however, no change in binding was observed as a result of the different storage conditions.

In some cases, fresh human leukocytes were prepared from whole blood collected in acid citrate dextrose. Red blood cells were removed by dextran sedimentation and the leukocyte-rich layer was harvested and treated as described above. Finally, purified neutrophil and mononuclear leukocytes (including monocytes and lymphocytes) were prepared by resuspending the leukocyte-rich layer of cells in autologous plasma and layering the cells over Lymphocyte Separation Medium (LSM; Organon Technika) followed by centrifugation (700×g, 30 minutes). The neutrophil enriched pellet and the mononuclear cells present at the density interface were washed in ice cold PBS and membranes were prepared as described above. A stained Cytospin (Shandon) preparation indicated that the neutrophil preparation was greater than 95% pure, and that the mononuclear preparation contained approximately 40%–50% monocytes.

Preparation of Membranes from Cell Lines

Non-adherent cell lines were collected by centrifugation (500×g, 7 minutes), washed in ice cold PBS, and the membranes were prepared as described above. Lightly adherent cell lines were washed with ice cold PBS and removed by gentle scraping with a cell scraper (Costar). Greater than 90% of the cells maintained viability during this procedure as determined by dye exclusion. Cells were resuspended in PBS and protease inhibitors. Tightly adherent cells were washed with ice cold PBS, then incubated with PBS plus the protease inhibitors described above. Cells were then removed by scraping and collected by centrifugation (500×g, 7 minutes). Membranes from adherent cells were then prepared as described above.

Binding Assay (Oil/Sucrose Method)

Membranes were diluted to 2 to 5 mg/ml in HBSS with and without 1 mg/ml BSA. The reaction mixture consisted of 280 $\mu$l membranes (2–4 mg/ml final concentration), 35 $\mu$l saline or test sample (in various concentrations), and 35 $\mu$l radioactively labeled underivatized, aqueous soluble $\beta$(1–3)-glucan (1 $\mu$g/ml final concentration). Binding was allowed to proceed for 60 to 120 minutes at 37° C. At the end of the incubation, 100 $\mu$l aliquots of reaction mixture were layered on top of a double layer density gradient consisting of 100 $\mu$l dibutyl phthalate (lower layer) and 100 $\mu$l 8% sucrose in PBS (upper layer) in 400 $\mu$l centrifuge tubes (Brinkman). The tubes were spun at 15,000×g for 4–5 minutes and the tips containing the membrane pellets were removed, incubated in 300 $\mu$l SOLVABLE™ (New England Nuclear, Boston, Mass.) overnight at 50° C. to dissolve the pellet, and then radioactivity determined by liquid scintillation counting. No radioactivity was found in the oil layer in the absence of added membranes. Alternatively, membranes were centrifuged directly in their incubation tubes at 15,000×g for 4–5 minutes at 37° C., the pellet washed with HBSS, then pellets solubilized and radioactivity determined by liquid scintillation counting.

Binding Assay (Non-Oil/Sucrose Method)

An alternative procedure to that using the oil/sucrose gradient involved centrifuging 100 $\mu$l aliquots of the binding assay in microfuge tubes at 12,000×g, for five minutes, followed by rinsing the resultant pellet with HBSS. Pellets were then dissolved in SOLVABLE™ and radioactively determined as above.

Extraction of Membranes with Chloroform/Methanol/Buffer

Human leukocyte membranes (5 mg protein/ml) prepared as described above were vortexed with 5 volumes of 3:2 chloroform/methanol (by volume) and centrifuged at 1,500×g to separate phases. The upper aqueous and lower organic phases were removed from the proteinaceous interphase, combined, and concentrated under a stream of Argon to approximately 50 $\mu$l. The residue was resuspended in HBSS, sonicated briefly, and centrifuged (12,000×g, 10 minutes) to pellet membranes. The pellet was resuspended in 500 $\mu$l HBSS and 100 $\mu$l was used per 350 $\mu$l binding assay. Assays for protein using the BCA reagent (Pierce) indicated that approximately 85% of the protein was removed from the resuspended fraction.

Electrophoretic Mobility Shift Assay (EMSA) (Murine)

BMC2.3 cells in DMEM plus 10% fetal calf serum were incubated with 3 $\mu$g/ml underivatized, aqueous soluble $\beta$(1–3)-glucan for various lengths of time. Nuclear extracts were prepared by the method of Dignam et al. (*Nuc. Acid Res.* 11:1475–1489 (1983)). Nuclear extracts were then incubated with $^{32}$P-labeled DNA oligonucleotide for twenty minutes at room temperature. The sequence of the oligonucleotide used as the probe was AGTTGAGGG-GACTTTCCCAGGC (SEQ ID NO: 1). The reaction mixture was then separated on a 4% polyacrylamide gel and the results recorded autoradiographically.

Electrophoretic Mobility Shift Assay (EMSA) (Human)

Human neutrophils (4.5×10$^6$ cells/ml; 10 ml total) purified as described above were incubated in RPMI+10% FCS (Sigma Chemical Co.) for 30 minutes at 37° C. Underivatized, aqueous soluble $\beta$(1–3)-glucan or dextran (both at 3 $\mu$g/ml) were then added and incubation continued an additional 60 minutes at 37° C. Nothing was added to control cells. At the end of the incubation, cells were washed in ice cold PBS+20 mM EDTA and nuclear extracts prepared and EMSAs performed as described above.

Purification of Lactosyl Ceramide (LacCer) from Human Leukocyte Membranes (HLM)

1. Extraction of Membranes with Chloroform/Methanol/Buffer

HLM (15 mg protein) in 1 mL of HBSS were extracted with chloroform (3 mL) and methanol (2 mL) by vortexing for one minute, followed by centrifugation at 1500×g for 10 minutes to separate the layers. The upper layer and proteinaceous interphase were discarded. The lower layer was dried under a stream of argon, and resuspended in 200 µL chloroform/methanol (10:1).

2. Thin Layer Chromatography Analysis of LacCer

Samples to be analyzed were spotted onto HPTLC silica gel plates and run in chloroform/methanol/water (80:20:2), along with commercially available LacCer standards. LacCer was visualized with the orcinol spray reagent (Schnaar, *Methods in Enzymology* 230:380 (Academic Press, 1994).

3. Silica Gel Chromatography

100 µL of the above extract was applied to a silica gel column (2 mL, 60 angstroms, 200–400 mesh) equilibrated in chloroform. The column was washed with chloroform (8 mL), then acetone (16 mL), followed by elution of a glycosphingolipid fraction with acetone/methanol (9:1, 16 mL). The acetone/methanol fraction was concentrated to dryness, and resuspended in acetone/methanol (10:1).

4. DEAE-Sephadex Chromatography

The acetone/methanol fraction from silica chromatography was applied to a DEAE-Sephadex A-25 column (1 mL resin in the acetate form, prepared in chloroform/methanol (1:2)). The column was washed with 60 mL chloroform/methanol (1:2). Neutral glycosphingolipids were contained in this fraction, which was dried and resuspended in chloroform/methanol (5:1).

5. Final Silica Gel Chromatography

Fractions from DEAE-Sephadex were applied to a Silica gel column (25×0.8 cm) equilibrated in chloroform. The column was washed with chloroform (60 mL), then chloroform/methanol (7.5:1) (60 mL). LacCer was eluted with 5 chloroform/methanol (5:1) (60 mL), then chloroform/methanol (2:1) (60 mL).

6. HPLC Fractionation

Fractionation of LacCer into individual components was carried out on a Hewlett Packard 1090 HPLC using a reverse-phase Symmetry C18 column (3.9×150 mm, Waters Associate, Milford, Mass.) and a mobile phase of 3.5% 0.2 M ammonium acetate in methanol at a flow rate of 1 mL/min. Peaks with u.v. absorbance at 206 nm were collected, dried down, and analyzed by TLC to identify fractions containing LacCer. Isolated fractions were quantitated using a S.E.D.E.R.E. Sedex 55 evaporative mass detector (Alfortville France) at 45° C.

7. GC-MS Analysis

Three different analyses were performed on each isolated LacCer fraction. An aliquot was methanolyzed and the methanol solution extracted with hexane. The extracted fatty-acid methyl esters were analyzed by GC-MS (Irie et al., *J. Biochem.* 108:531–536 (1990). The methanol layer was dried, trimethylsilylated, and dissolved in hexane. The resulting trimethylsilylated methyl glycosides were analyzed by GC-MS (Irie et al., 1990). A second aliquot was treated with ceramide glycanase (see below) and freeze dried. The resulting acylated sphingosine and oligosaccharide were trimethylsilylated, dissolved in hexane, and analyzed by GC-MS on a HT-5 aluminum-clad capillary column.

Binding Assay in Reconstituted Membranes

Membranes were prepared from the receptor-negative cell line, U937, and extracted with chloroform/methanol as described above. The upper and lower layers were combined after removal of the proteinaceous interphase and dried under a stream of argon with the sample to be assayed for binding (lactosyl ceramide or fractions from the purification).

Alternatively, a mixture of purified phospholipids were dried with the sample for use in the binding assay. The phospholipid mixture contained phosphatidylcholine (132 µg), phosphatidylethanolamine (112 µg), phosphatidylinositol (36 µg), and phosphatidylserine (56 µg).

The dried lipid/sample preparations were resuspended in HBSS (500 µL) by brief sonication, and centrifuged for 10 minutes at 12,000×g. The supernatants from this spin were discarded, and the pellets were resuspended in HBSS (560 µL). Aliquots of 280 µL were added to tubes containing saline (35 µL) or unlabelled, underivatized, aqueous soluble β(1–3)-glucan (35 µL of 10 mg/mL stock), and $^3$H-underivatized, aqueous soluble β(1–3) glucan (35 µL of a 10 µg/mL stock). Assays were incubated at 37° C. for one hour, after which time three 100 µL aliquots were removed and centrifuged in microfuge tubes at 12,000×g for 5 minutes at room temperature. The supernatants were discarded and the pellets were rinsed with 150 µL of HBSS. Pellets were then dissolved in SOLVABLE™, scintillation fluid was added, and radioactivity was measured.

Binding Assay in 96-Well Plates

Lactosyl ceramide or the sample to be measured was suspended in ethanol. Aliquots as specified were added in triplicate to the wells of a 96-well plate and air dried. The following components were premixed, then 100 µL was added to each well: saline (10 µL) or unlabelled, underivatized, aqueous soluble β(1–3)-glucan (10 µL of a 10 mg/ml stock), $^3$H-underivatized, aqueous soluble β(1–3) glucan (10 µL of a 10 µg/ml stock), and HBSS (80 µL). Plates were incubated at 37° C. for 1.5 to 2 hours, then supernatants were removed from each well and discarded. Wells were rinsed with HBSS (200 µL) and SOLVABLE™ (100 µL) was added. The plate was incubated at 60° C. for 5 minutes, then supernatants were removed and counted.

While this invention has been particularly shown and described with references to preferred embodiments thereof, it will be understood by those skilled in the art that various changes in form and details may be made therein without departing from the spirit and scope of the invention as defined by the appended claims.

We claim:

1. An assay for assessing the affinity of a carbohydrate for a glycolipid, comprising the steps of:
   a) combining a glycolipid and a carbohydrate under conditions suitable for interaction between the carbohydrate and the glycolipid;
   b) determining the affinity of the carbohydrate for the glycolipid; and
   c) comparing the affinity determined in (b) with the affinity in the presence of competitor carbohydrate or glycolipid, thereby assessing the affinity of the carbohydrate for a glycolipid.

2. An assay according to claim 1, wherein the glycolipid is LacCer.

3. An assay according to claim 1, wherein the carbohydrate is underivatized, aqueous soluble $\beta(1-3)$-glucan.

* * * * *

SEQUENCE LISTING

<160> NUMBER OF SEQ ID NOS: 1

<210> SEQ ID NO 1
<211> LENGTH: 22
<212> TYPE: DNA
<213> ORGANISM: Artificial Sequence
<220> FEATURE:
<223> OTHER INFORMATION: Oligonucleotide probe

```
-continued

<400> SEQUENCE: 1
agttgagggg actttcccag gc                                              22
```